(12) United States Patent
Florence et al.

(10) Patent No.: US 10,202,444 B2
(45) Date of Patent: Feb. 12, 2019

(54) ANTI-TAU ANTIBODIES

(71) Applicant: rPeptide LLC, Bogart, GA (US)

(72) Inventors: Quentin Florence, Loganville, GA (US); Nanda Menon, Athens, GA (US); William Moffitt, Alexandria, VA (US); Bill Lunsford, III, Athens, GA (US)

(73) Assignee: rPeptide, LLC, Watkinsville, GA (US)

(*) Notice: Subject to any disclaimer, the term of this patent is extended or adjusted under 35 U.S.C. 154(b) by 0 days.

(21) Appl. No.: 15/552,633

(22) PCT Filed: Feb. 23, 2016

(86) PCT No.: PCT/US2016/019067
§ 371 (c)(1),
(2) Date: Aug. 22, 2017

(87) PCT Pub. No.: WO2016/137950
PCT Pub. Date: Sep. 1, 2016

(65) Prior Publication Data
US 2018/0051073 A1    Feb. 22, 2018

Related U.S. Application Data

(60) Provisional application No. 62/120,120, filed on Feb. 24, 2015.

(51) Int. Cl.
*C07K 16/18* (2006.01)
*G01N 33/68* (2006.01)
*A61K 49/00* (2006.01)

(52) U.S. Cl.
CPC ......... *C07K 16/18* (2013.01); *A61K 49/0002* (2013.01); *G01N 33/6896* (2013.01); *C07K 2317/14* (2013.01); *C07K 2317/21* (2013.01); *C07K 2317/24* (2013.01); *C07K 2317/34* (2013.01); *C07K 2317/56* (2013.01); *C07K 2317/565* (2013.01); *G01N 2333/47* (2013.01); *G01N 2800/28* (2013.01)

(58) Field of Classification Search
None
See application file for complete search history.

(56) References Cited

U.S. PATENT DOCUMENTS

| 2004/0157214 A1 | 8/2004 | McCafferty et al. |
| 2009/0136495 A1 | 5/2009 | Gately et al. |
| 2009/0269850 A1 | 10/2009 | Kaneda et al. |
| 2013/0295021 A1 | 11/2013 | Chen et al. |

FOREIGN PATENT DOCUMENTS

| CN | 102070718 A | 5/2011 |
| WO | 2011094645 A1 | 8/2011 |
| WO | 2014/100079 A1 | 6/2014 |
| WO | 2014/100600 A2 | 6/2014 |
| WO | 2014/165271 A2 | 10/2014 |

OTHER PUBLICATIONS

Chen "Enhancement and destruction of antibody function by somatic mutation: unequal occurrence is controlled by V gene combinatorial associations" The EMBO Journal vol. 14 No. 1 2 pp. 2784-2794 (Year: 1995).*
Kussie "A Single Engineered Amino Acid Substitution Changes Antibody Fine Specificity" J immunol 152(1):146-52 (Year: 1994).*
Bradbury et al., "Standardize antibodies used in research," Nature (Feb. 5, 2015); 518:27-29.
Chen et al., "Preperation of human tau exon-2 and -10-specific monoclonal antibodies for the recognition of brain tau proteins in various mammals," International Journal of Molecular Medicine (2015); 36:455-462.

* cited by examiner

*Primary Examiner* — Adam Weidner
(74) *Attorney, Agent, or Firm* — Fox Rothschild LLP

(57) ABSTRACT

The present invention relates, in part, to isolated antibodies that specifically interact with and show measurable binding affinity to an epitope of the tau protein. Such antibodies may be used for the modulation of tau activity and/or aggregation, to study the effects of the tau protein on cell function and, in certain embodiments, for the treatment and/or prevention of a disease or condition associated with neurodegenerative tauopathy.

20 Claims, 7 Drawing Sheets
Specification includes a Sequence Listing.

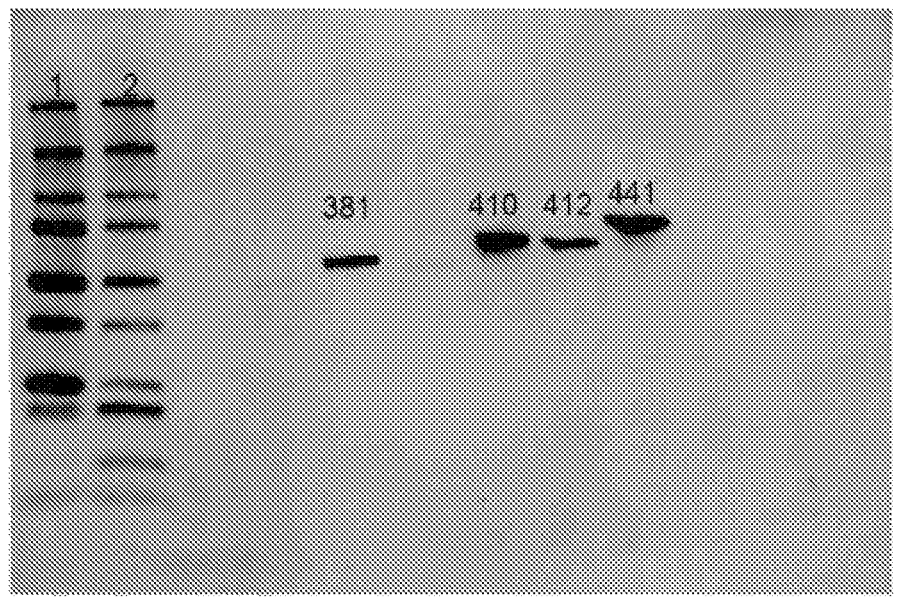
Figure 2A - 4G11 mAb
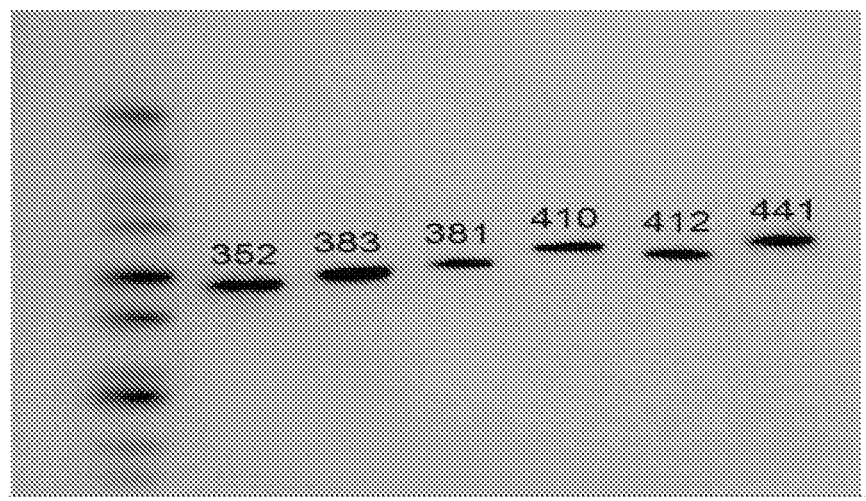
Figure 2B – 1A6 mAb

MAEPRQEFEVMEDHAGTYGLGDRKDQGGYTMHQDQEGDTDAGLKESPLQTPTEDG N1

N2
SEEPGSETSDAKSTPTAEDVTAPLVDEGAPGKQAAAQPHTEIPEGTTAEEAGIGDTPS

LEDEAAGHVTQARMVSKSKDGTGSDDKKAKGADGKTKIATPRGAAPPGQKGQANA

TRIPAKTPPAPKTPPSSGEPPKSGDRSGYSSPGSPGTPGSRSRTPSLPTPPTREPKKVAV

R1 R2
VRTPPKSPSSAKSRLQTAPVPMPDLKNVKSKIGSTENLKHQPGGGKVQIINKKLDLSN

R3
VQSKCGSKDNIKHVPGGGSVQIVYKPVDLSKVTSKCGSLGNIHHKPGGGQEVKSE

R4
KLDFKDRVQSKIGSLDNITHVPGGGNKKIETHKLTFRENAKAKTDHGAEIVYKSPVV

SGDTSPRHLSNVSSTGSIDMVDSPQLATLADEVSASLAKQGL (SEQ ID NO: 6)

Figure 5

SEQUENCE LISTING

<160> NUMBER OF SEQ ID NOS: 52

<210> SEQ ID NO 1
<211> LENGTH: 352
<212> TYPE: PRT
<213> ORGANISM: Homo sapiens

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

```
Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Val Tyr Lys Pro Val
    210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr
        275                 280                 285

Phe Arg Glu Asn Ala Lys Ala Lys Thr Asp His Gly Ala Glu Ile Val
    290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350

<210> SEQ ID NO 2
<211> LENGTH: 383
<212> TYPE: PRT
<213> ORGANISM: Homo sapiens

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Ala Glu Glu Ala
            35                  40                  45

Gly Ile Gly Asp Thr Pro Ser Leu Glu Asp Glu Ala Ala Gly His Val
        50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190
```

Pro Asp Leu Lys Asn Val Lys Ser Lys Ile Gly Ser Thr Glu Asn Leu
            195                 200                 205

Lys His Gln Pro Gly Gly Gly Lys Val Gln Ile Ile Asn Lys Lys Leu
        210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
        290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
        355                 360                 365

Thr Leu Ala Asp Glu Val Ser Ala Ser Leu Ala Lys Gln Gly Leu
        370                 375                 380

<210> SEQ ID NO 3
<211> LENGTH: 381
<212> TYPE: PRT
<213> ORGANISM: Homo sapiens

<400> SEQUENCE: 3

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

```
Glu Pro Lys Lys Val Ala Val Val Arg Thr Pro Pro Lys Ser Pro Ser
            195                 200                 205
Ser Ala Lys Ser Arg Leu Gln Thr Ala Pro Val Pro Met Pro Asp Leu
    210                 215                 220
Lys Asn Val Lys Ser Lys Ile Gly Ser Thr Glu Asn Leu Lys His Gln
225                 230                 235                 240
Pro Gly Gly Gly Lys Val Gln Ile Val Tyr Lys Pro Val Asp Leu Ser
                245                 250                 255
Lys Val Thr Ser Lys Cys Gly Ser Leu Gly Asn Ile His His Lys Pro
            260                 265                 270
Gly Gly Gly Gln Val Glu Val Lys Ser Glu Lys Leu Asp Phe Lys Asp
        275                 280                 285
Arg Val Gln Ser Lys Ile Gly Ser Leu Asp Asn Ile Thr His Val Pro
    290                 295                 300
Gly Gly Gly Asn Lys Lys Ile Glu Thr His Lys Leu Thr Phe Arg Glu
305                 310                 315                 320
Asn Ala Lys Ala Lys Thr Asp His Gly Ala Glu Ile Val Tyr Lys Ser
                325                 330                 335
Pro Val Val Ser Gly Asp Thr Ser Pro Arg His Leu Ser Asn Val Ser
            340                 345                 350
Ser Thr Gly Ser Ile Asp Met Val Asp Ser Pro Gln Leu Ala Thr Leu
        355                 360                 365
Ala Asp Glu Val Ser Ala Ser Leu Ala Lys Gln Gly Leu
    370                 375                 380

<210> SEQ ID NO 4
<211> LENGTH: 412
<212> TYPE: PRT
<213> ORGANISM: Homo sapiens

<400> SEQUENCE: 4

Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
            20                  25                  30
Gln Asp Gln Glu Gly Asp Thr Asp Ala Gly Leu Lys Glu Ser Pro Leu
        35                  40                  45
Gln Thr Pro Thr Glu Asp Gly Ser Glu Glu Pro Gly Ser Glu Thr Ser
    50                  55                  60
Asp Ala Lys Ser Thr Pro Thr Ala Glu Ala Glu Glu Ala Gly Ile Gly
65                  70                  75                  80
Asp Thr Pro Ser Leu Glu Asp Glu Ala Ala Gly His Val Thr Gln Ala
                85                  90                  95
Arg Met Val Ser Lys Ser Lys Asp Gly Thr Gly Ser Asp Asp Lys Lys
            100                 105                 110
Ala Lys Gly Ala Asp Gly Lys Thr Lys Ile Ala Thr Pro Arg Gly Ala
        115                 120                 125
Ala Pro Pro Gly Gln Lys Gly Gln Ala Asn Ala Thr Arg Ile Pro Ala
    130                 135                 140
Lys Thr Pro Pro Ala Pro Lys Thr Pro Pro Ser Ser Gly Glu Pro Pro
145                 150                 155                 160
Lys Ser Gly Asp Arg Ser Gly Tyr Ser Ser Pro Gly Ser Pro Gly Thr
                165                 170                 175
Pro Gly Ser Arg Ser Arg Thr Pro Ser Leu Pro Thr Pro Pro Thr Arg
            180                 185                 190
```

```
Glu Pro Lys Lys Val Ala Val Val Arg Thr Pro Pro Lys Ser Pro Ser
            195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
                260                 265                 270

Gly Gly Gly Ser Val Gln Ile Val Tyr Lys Pro Val Asp Leu Ser Lys
            275                 280                 285

Val Thr Ser Lys Cys Gly Ser Leu Gly Asn Ile His His Lys Pro Gly
    290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
                340                 345                 350

Ala Lys Ala Lys Thr Asp His Gly Ala Glu Ile Val Tyr Lys Ser Pro
            355                 360                 365

Val Val Ser Gly Asp Thr Ser Pro Arg His Leu Ser Asn Val Ser Ser
    370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
                405                 410

<210> SEQ ID NO 5
<211> LENGTH: 410
<212> TYPE: PRT
<213> ORGANISM: Homo sapiens

<400> SEQUENCE: 5

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160
```

Gly Gln Lys Gly Gln Ala Asn Ala Thr Arg Ile Pro Ala Lys Thr Pro
                165                 170                 175

Pro Ala Pro Lys Thr Pro Ser Ser Gly Glu Pro Lys Ser Gly
            180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
                260                 265                 270

Gly Lys Val Gln Ile Val Tyr Lys Pro Val Asp Leu Ser Lys Val Thr
                275                 280                 285

Ser Lys Cys Gly Ser Leu Gly Asn Ile His His Lys Pro Gly Gly Gly
            290                 295                 300

Gln Val Glu Val Lys Ser Glu Lys Leu Asp Phe Lys Asp Arg Val Gln
305                 310                 315                 320

Ser Lys Ile Gly Ser Leu Asp Asn Ile Thr His Val Pro Gly Gly Gly
                325                 330                 335

Asn Lys Lys Ile Glu Thr His Lys Leu Thr Phe Arg Glu Asn Ala Lys
                340                 345                 350

Ala Lys Thr Asp His Gly Ala Glu Ile Val Tyr Lys Ser Pro Val Val
                355                 360                 365

Ser Gly Asp Thr Ser Pro Arg His Leu Ser Asn Val Ser Ser Thr Gly
    370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
                405                 410

<210> SEQ ID NO 6
<211> LENGTH: 441
<212> TYPE: PRT
<213> ORGANISM: Homo sapiens

<400> SEQUENCE: 6

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

```
Ser Lys Ser Lys Asp Gly Thr Gly Ser Asp Asp Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440

<210> SEQ ID NO 7
<211> LENGTH: 8
<212> TYPE: PRT
<213> ORGANISM: Homo sapiens

<400> SEQUENCE: 7

Glu Glu Pro Gly Ser Glu Thr Ser
1               5

<210> SEQ ID NO 8
<211> LENGTH: 11
<212> TYPE: PRT
<213> ORGANISM: Homo sapiens
```

<400> SEQUENCE: 8

Glu Phe Glu Val Met Glu Asp His Ala Gly Thr
1               5                   10

<210> SEQ ID NO 9
<211> LENGTH: 6
<212> TYPE: PRT
<213> ORGANISM: Homo sapiens

<400> SEQUENCE: 9

Leu Pro Thr Pro Pro Thr
1               5

<210> SEQ ID NO 10
<211> LENGTH: 7
<212> TYPE: PRT
<213> ORGANISM: Mus musculus

<400> SEQUENCE: 10

Gly Phe Thr Phe Asn Ile Tyr
1               5

<210> SEQ ID NO 11
<211> LENGTH: 8
<212> TYPE: PRT
<213> ORGANISM: Mus musculus

<400> SEQUENCE: 11

Arg Ser Lys Ser Asn Asn Tyr Ala
1               5

<210> SEQ ID NO 12
<211> LENGTH: 8
<212> TYPE: PRT
<213> ORGANISM: Mus musculus

<400> SEQUENCE: 12

His Gly Asn Tyr Tyr Phe Asp Tyr
1               5

<210> SEQ ID NO 13
<211> LENGTH: 5
<212> TYPE: PRT
<213> ORGANISM: Mus musculus

<400> SEQUENCE: 13

Ile Tyr Ala Met Asn
1               5

<210> SEQ ID NO 14
<211> LENGTH: 19
<212> TYPE: PRT
<213> ORGANISM: Mus musculus

<400> SEQUENCE: 14

Arg Ile Arg Ser Lys Ser Asn Asn Tyr Ala Thr Tyr Tyr Ala Asp Ser
1               5                   10                  15

Met Lys Asp

<210> SEQ ID NO 15
<211> LENGTH: 12
<212> TYPE: PRT
<213> ORGANISM: Mus musculus

```
<400> SEQUENCE: 15

Ser Ala Asp Ser Ser Val Ser Ser Ser Tyr Leu Asn
1               5                   10

<210> SEQ ID NO 16
<211> LENGTH: 7
<212> TYPE: PRT
<213> ORGANISM: Mus musculus

<400> SEQUENCE: 16

Arg Thr Ser Asn Leu Ala Ser
1               5

<210> SEQ ID NO 17
<211> LENGTH: 11
<212> TYPE: PRT
<213> ORGANISM: Mus musculus

<400> SEQUENCE: 17

Gln Gln Trp Ser Gly Tyr Pro Phe Ile Phe Thr
1               5                   10

<210> SEQ ID NO 18
<211> LENGTH: 7
<212> TYPE: PRT
<213> ORGANISM: Mus musculus

<400> SEQUENCE: 18

Gly Phe Thr Phe Ser Ser Phe
1               5

<210> SEQ ID NO 19
<211> LENGTH: 6
<212> TYPE: PRT
<213> ORGANISM: Mus musculus

<400> SEQUENCE: 19

Ser Ser Gly Ser Ser Thr
1               5

<210> SEQ ID NO 20
<211> LENGTH: 9
<212> TYPE: PRT
<213> ORGANISM: Mus musculus

<400> SEQUENCE: 20

Asn Gln Ser Pro Thr Gly Phe Ala Tyr
1               5

<210> SEQ ID NO 21
<211> LENGTH: 5
<212> TYPE: PRT
<213> ORGANISM: Mus musculus

<400> SEQUENCE: 21

Ser Phe Gly Met His
1               5

<210> SEQ ID NO 22
<211> LENGTH: 17
<212> TYPE: PRT
<213> ORGANISM: Mus musculus
```

```
<400> SEQUENCE: 22

Tyr Ile Ser Ser Gly Ser Ser Thr Ile Tyr Tyr Ala Asp Thr Val Lys
1               5                   10                  15

Gly

<210> SEQ ID NO 23
<211> LENGTH: 16
<212> TYPE: PRT
<213> ORGANISM: Mus musculus

<400> SEQUENCE: 23

Arg Ser Ser Gln Ser Leu Val His Ser Asn Gly Asn Thr Tyr Leu His
1               5                   10                  15

<210> SEQ ID NO 24
<211> LENGTH: 7
<212> TYPE: PRT
<213> ORGANISM: Mus musculus

<400> SEQUENCE: 24

Lys Val Ser Asn Arg Phe Ser
1               5

<210> SEQ ID NO 25
<211> LENGTH: 9
<212> TYPE: PRT
<213> ORGANISM: Mus musculus

<400> SEQUENCE: 25

Ser Gln Ser Thr His Val Pro Leu Thr
1               5

<210> SEQ ID NO 26
<211> LENGTH: 21
<212> TYPE: DNA
<213> ORGANISM: Mus musculus

<400> SEQUENCE: 26
ggattcacct tcaatatcta c                                         21

<210> SEQ ID NO 27
<211> LENGTH: 24
<212> TYPE: DNA
<213> ORGANISM: Mus musculus

<400> SEQUENCE: 27
agaagtaaaa gtaataatta tgca                                      24

<210> SEQ ID NO 28
<211> LENGTH: 24
<212> TYPE: DNA
<213> ORGANISM: Mus musculus

<400> SEQUENCE: 28
catggtaact actactttga ctac                                      24

<210> SEQ ID NO 29
<211> LENGTH: 15
<212> TYPE: DNA
<213> ORGANISM: Mus musculus

<400> SEQUENCE: 29
atctacgcca tgaac                                                15
```

```
<210> SEQ ID NO 30
<211> LENGTH: 57
<212> TYPE: DNA
<213> ORGANISM: Mus musculus

<400> SEQUENCE: 30
cgcataagaa gtaaaagtaa taattatgca acatattatg ccgattcaat gaaagac       57

<210> SEQ ID NO 31
<211> LENGTH: 36
<212> TYPE: DNA
<213> ORGANISM: Mus musculus

<400> SEQUENCE: 31
agtgccgact caagtgtaag ttccagttac ttgaac                              36

<210> SEQ ID NO 32
<211> LENGTH: 21
<212> TYPE: DNA
<213> ORGANISM: Mus musculus

<400> SEQUENCE: 32
aggacatcca acctggcttc t                                              21

<210> SEQ ID NO 33
<211> LENGTH: 33
<212> TYPE: DNA
<213> ORGANISM: Mus musculus

<400> SEQUENCE: 33
cagcagtgga gtggttaccc attcatattc acg                                 33

<210> SEQ ID NO 34
<211> LENGTH: 21
<212> TYPE: DNA
<213> ORGANISM: Mus musculus

<400> SEQUENCE: 34
ggattcactt tcagtagctt t                                              21

<210> SEQ ID NO 35
<211> LENGTH: 18
<212> TYPE: DNA
<213> ORGANISM: Mus musculus

<400> SEQUENCE: 35
agtagtggca gtagtacc                                                  18

<210> SEQ ID NO 36
<211> LENGTH: 27
<212> TYPE: DNA
<213> ORGANISM: Mus musculus

<400> SEQUENCE: 36
aaccaatccc ctacggggtt tgcttac                                        27

<210> SEQ ID NO 37
<211> LENGTH: 15
<212> TYPE: DNA
<213> ORGANISM: Mus musculus

<400> SEQUENCE: 37
agctttggaa tgcac                                                     15
```

<210> SEQ ID NO 38
<211> LENGTH: 51
<212> TYPE: DNA
<213> ORGANISM: Mus musculus

<400> SEQUENCE: 38
tacattagta gtggcagtag taccatctac tatgcagaca cagtgaaggg c        51

<210> SEQ ID NO 39
<211> LENGTH: 48
<212> TYPE: DNA
<213> ORGANISM: Mus musculus

<400> SEQUENCE: 39
agatctagtc agagccttgt acacagtaat ggaaacacct atttacat           48

<210> SEQ ID NO 40
<211> LENGTH: 21
<212> TYPE: DNA
<213> ORGANISM: Mus musculus

<400> SEQUENCE: 40
aaagtttcca accgattttc t                                         21

<210> SEQ ID NO 41
<211> LENGTH: 27
<212> TYPE: DNA
<213> ORGANISM: Mus musculus

<400> SEQUENCE: 41
tctcaaagta cacatgttcc tctcacg                                   27

<210> SEQ ID NO 42
<211> LENGTH: 119
<212> TYPE: PRT
<213> ORGANISM: Mus musculus

<400> SEQUENCE: 42

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Ile Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Met Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Tyr Tyr Phe Asp Tyr Trp Gly Gln Gly
            100                 105                 110

Thr Thr Leu Thr Val Ser Ser
        115

<210> SEQ ID NO 43
<211> LENGTH: 357
<212> TYPE: DNA
<213> ORGANISM: Mus musculus

<400> SEQUENCE: 43

```
gaggtgcagc ttgttgagtc tggtggagga ttggtgcagc ctaaagggtc attgaaactc        60
tcatgtgcag cctctggatt caccttcaat atctacgcca tgaactgggt ccgccaggct      120
ccaggaaagg gtttggaatg ggttgctcgc ataagaagta aagtaataa ttatgcaaca       180
tattatgccg attcaatgaa agacaggttc accatctcca gagatgattc acaaagcatg     240
ctctatctgc aaatgaacaa cttgaaaact gaggacacag ccatgtatta ctgtgtgaga      300
catggtaact actactttga ctactggggc caaggcacca ctctcacagt ctcctca         357
```

<210> SEQ ID NO 44
<211> LENGTH: 110
<212> TYPE: PRT
<213> ORGANISM: Mus musculus

<400> SEQUENCE: 44

```
Glu Asn Val Leu Thr Gln Ser Pro Ala Ile Met Ala Ala Ser Leu Gly
1               5                   10                  15
Gln Lys Val Thr Met Thr Cys Ser Ala Asp Ser Ser Val Ser Ser Ser
                20                  25                  30
Tyr Leu Asn Trp Tyr Gln Gln Lys Ser Gly Ala Ser Pro Lys Pro Leu
            35                  40                  45
Ile His Arg Thr Ser Asn Leu Ala Ser Gly Val Pro Ala Arg Phe Ser
        50                  55                  60
Gly Ser Gly Ser Gly Thr Ser Tyr Ser Leu Thr Ile Ser Ser Val Glu
65                  70                  75                  80
Ala Glu Asp Asp Ala Thr Tyr Tyr Cys Gln Gln Trp Ser Gly Tyr Pro
                85                  90                  95
Phe Ile Phe Thr Phe Gly Ser Gly Thr Lys Leu Glu Ile Lys
            100                 105                 110
```

<210> SEQ ID NO 45
<211> LENGTH: 330
<212> TYPE: DNA
<213> ORGANISM: Mus musculus

<400> SEQUENCE: 45

```
gaaaatgtgc tcacccagtc tccagcaata atggctgcct ctctggggca gaaggtcacc        60
atgacctgca gtgccgactc aagtgtaagt tccagttact tgaactggta ccagcagaag      120
tcaggcgctt cccccaaacc cttgattcat aggacatcca acctggcttc tggagtccca     180
gctcgcttca gtggcagtgg gtctgggacc tcttactctc tcacaatcag cagcgtggag    240
gctgaagatg atgcaactta ttactgccag cagtggagtg gttacccatt catattcacg     300
ttcggctcgg ggacaaagtt ggaaataaaa                                                  330
```

<210> SEQ ID NO 46
<211> LENGTH: 118
<212> TYPE: PRT
<213> ORGANISM: Mus musculus

<400> SEQUENCE: 46

```
Asp Val Gln Leu Val Glu Ser Gly Gly Gly Leu Val Gln Pro Gly Gly
1               5                   10                  15
Ser Arg Lys Leu Ser Cys Ala Ala Ser Gly Phe Thr Phe Ser Ser Phe
                20                  25                  30
Gly Met His Trp Val Arg Gln Val Pro Glu Lys Gly Leu Glu Trp Val
            35                  40                  45
```

```
Ala Tyr Ile Ser Ser Gly Ser Ser Thr Ile Tyr Tyr Ala Asp Thr Val
        50                  55                  60

Lys Gly Arg Phe Thr Ile Ser Arg Asp Asn Pro Lys Asn Thr Leu Phe
 65                  70                  75                  80

Leu Gln Met Thr Ser Leu Arg Ser Glu Asp Thr Ala Met Tyr Tyr Cys
                 85                  90                  95

Ala Ser Asn Gln Ser Pro Thr Gly Phe Ala Tyr Trp Gly Gln Gly Thr
            100                 105                 110

Leu Val Thr Val Ser Ala
        115
```

<210> SEQ ID NO 47
<211> LENGTH: 354
<212> TYPE: DNA
<213> ORGANISM: Mus musculus

<400> SEQUENCE: 47

```
gatgtgcagc tggtggagtc tgggggaggc ttagtgcagc ctggagggtc ccggaaactc      60
tcctgtgcag cctctggatt cactttcagt agctttggaa tgcactgggt tcgtcaggtt     120
ccagagaagg ggctggagtg ggtcgcatac attagtagtg gcagtagtac catctactat     180
gcagacacag tgaagggccg attcaccatc tccagagaca atcccaagaa caccctgttc     240
ctgcaaatga ccagtctaag gtctgaggac acggccatgt attactgtgc aagtaaccaa     300
tcccctacgg ggtttgctta ctggggccaa gggactctgg tcactgtctc tgca           354
```

<210> SEQ ID NO 48
<211> LENGTH: 112
<212> TYPE: PRT
<213> ORGANISM: Mus musculus

<400> SEQUENCE: 48

```
Asp Val Val Met Thr Gln Thr Pro Leu Ser Leu Pro Val Ser Leu Gly
  1               5                  10                  15

Asp Gln Ala Ser Ile Ser Cys Arg Ser Ser Gln Ser Leu Val His Ser
             20                  25                  30

Asn Gly Asn Thr Tyr Leu His Trp Tyr Leu Gln Lys Pro Gly Gln Ser
         35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Leu Thr Phe Gly Ala Gly Thr Lys Leu Glu Leu Lys
            100                 105                 110
```

<210> SEQ ID NO 49
<211> LENGTH: 336
<212> TYPE: DNA
<213> ORGANISM: Mus musculus

<400> SEQUENCE: 49

```
gatgttgtga tgacccaaac tccactctcc ctgcctgtca gtcttggaga tcaagcctcc      60
atctcttgca gatctagtca gagccttgta cacagtaatg gaaacaccta tttacattgg     120
tacctgcaga agccaggcca gtctccaaag ctcctaatct acaaagtttc caaccgattt     180
tctggggtcc cagacaggtt cagtggcagt ggatcaggga cagatttcac actcaagatc     240
```

```
agcagagtgg aggctgagga tctgggagtt tatttctgct ctcaaagtac acatgttcct    300
ctcacgttcg gtgctgggac caagctggag ctgaaa                              336

<210> SEQ ID NO 50
<211> LENGTH: 35
<212> TYPE: DNA
<213> ORGANISM: Mus musculus
<220> FEATURE:
<221> NAME/KEY: modified_base
<222> LOCATION: (30)..(30)
<223> OTHER INFORMATION: I
<220> FEATURE:
<221> NAME/KEY: misc_feature
<222> LOCATION: (30)..(30)
<223> OTHER INFORMATION: n is a, c, g, or t

<400> SEQUENCE: 50
cccaagcttc cagggrccar kggataracn grtgg                               35

<210> SEQ ID NO 51
<211> LENGTH: 30
<212> TYPE: DNA
<213> ORGANISM: Mus musculus

<400> SEQUENCE: 51
cccaagctta ctggatggtg ggaagatgga                                     30

<210> SEQ ID NO 52
<211> LENGTH: 32
<212> TYPE: DNA
<213> ORGANISM: Mus musculus
<220> FEATURE:
<221> NAME/KEY: modified_base
<222> LOCATION: (24)..(24)
<223> OTHER INFORMATION: I
<220> FEATURE:
<221> NAME/KEY: misc_feature
<222> LOCATION: (24)..(24)
<223> OTHER INFORMATION: n is a, c, g, or t

<400> SEQUENCE: 52
cccaagctta gctcytcwgw gganggyggr aa                                  32
```

ANTI-TAU ANTIBODIES

CROSS-REFERENCE TO RELATED APPLICATIONS

This application claims priority to U.S. provisional application Ser. No. 62/120,120, filed Feb. 24, 2015, the disclosure of which is incorporated herein by reference in its entirety.

FIELD OF THE INVENTION

The present invention relates, in part, to isolated antibodies, and fragments thereof, that specifically interact with and show measurable binding affinity to an epitope of a tau protein isoform. Such antibodies may be used for the modulation of tau activity or aggregation, to study its effects on cell function and, in certain embodiments, for the treatment, prevention, diagnosis and/or monitoring of a disease or condition associated with such proteins.

BACKGROUND OF THE INVENTION

The tau protein is a microtubule-associated protein expressed, primarily, in the central nervous system. Its main function is stabilization of microtubules in these cells. More specifically, tau proteins interact with tubulin to stabilize it within the cells and promote tubulin assembly into microtubules.

There are six major isoforms of tau proteins expressed in the adult human, which are distinguished by the number of binding domains present at either or both the C-terminus and/or N-terminus of the protein. Three isoforms have three binding domains and three isoforms have four binding domains. These isoforms are derived from a single gene by alternative splicing.

Under pathological conditions, the tau protein becomes hyper-phosphorylated, resulting in a loss of tubulin binding and destabilization of microtubules. This is often followed by the aggregation and deposition of tau in pathogenic neurofibrillary tangles.

A number of disorders are related to tau proteins, particularly protein misfolding disorders, and are characterized by such pathological conditions. One example of such a disease includes Alzheimer's disease (AD), where hyper-phosporylation of the tau protein results in the self-assembly of tangles of paired helical filaments and strategy filaments. The role of such filaments in the progression of the disease is currently being studied and is unclear.

Immunotherapies targeting the beta-amyloid peptide in AD have produced encouraging results in animal models and shown promise in clinical trials. In the wake of success of Aβ-based immunization therapy in transgenic animal models, the concept of active immunotherapy was expanded to the tau protein. Active vaccination of wild type mice using the tau protein was found, however, to induce the formation of neurofibrillary tangles, axonal damage and mononuclear infiltrates in the central nervous system, accompanied by neurologic deficits. Subsequent studies in transgenic mouse lines using active vaccination with phosphorylated tau peptides revealed reduced brain levels of tau aggregates in the brain and slowed progression of behavior impairments. These findings highlight the potential benefit but also the tremendous risks associated with active immunotherapy approaches targeting tau. Novel therapeutic strategies are urgently needed addressing pathological tau proteins with efficacious and safe therapy.

SUMMARY OF THE INVENTION

In certain aspects, the present invention relates to isolated antibodies or fragments thereof that specifically interact with and/or show measurable binding affinity to an epitope of the tau protein, including one or more of its six isoforms, as defined herein. In further aspects, such antibodies or fragments thereof specifically interact with and/or show measurable binding affinity to a polypeptide within or near one or more binding domains of the tau protein or a polypeptide substantially homologous thereto.

Antibodies of the present invention (collectively referred to as anti-tau antibodies) may include the entire antibody, a fragment or substantially homologous fragment of the monoclonal antibodies (mAbs) 4G11, any such fragment or substantially homologous fragment including but not limited to one, two, three, four, five or all six CDRs (as determined by either the Kabat and/or Chothia methodology, as described herein, as for example each of three CDRs from the variable light chain and/or each of three CDRs from the variable heavy chain) from the variable light chain and/or the variable heavy chain of the monoclonal antibody 4G11. Antibodies of the present invention may include the entire antibody, a fragment or substantially homologous fragment of the monoclonal antibody 1A6, any such fragment or substantially homologous fragment including but not limited to one, two, three, four, five or all six CDRs (as determined by either the Kabat and/or Chothia methodology, as described herein, as for example each of three CDRs from the variable light chain and/or each of three CDRs from the variable heavy chain) from the variable light chain and/or the variable heavy chain of the monoclonal antibody 1A6. Any such entire antibody, antibody fragment, or substantially homologous fragment (such as, but not limited to, a substantially homologous fragment containing one or more conservative amino acid substitutions) may be derived from the 4G12 antibody. Additionally, any such entire antibody, antibody fragment, or substantially homologous fragment (such as, but not limited to, a substantially homologous fragment containing one or more conservative amino acid substitutions) may be derived from the 1A6 antibody. Thus, fragments or substantially homologous fragments may include one or a portion of the variable light and heavy chain sequences or CDR regions of 4G11 and/or 1A6, or may be substantially homologous to such sequences. Any such antibody may take the form of a human monoclonal antibody, a humanized antibody, a chimeric antibody, an affinity matured antibody, a mutated antibody or any such antibody generated by methodology as known in the art. Light and heavy chain CDRs of each of 4G11 and 1A6 are as follows:

4G11

```
                                            (SEQ ID NO: 15)
A. Peptide-light chain-SADSSVSSSYLN (SEQ ID NO: 16)
(CDR1-Chothia and Kabat Methods), RTSNLAS (SEQ ID. NO.: 17)
(CDR2-Chothia and Kabat Methods), and QQWSGYPFIFT (CDR3-Chothia and Kabat Methods);

(SEQ ID NO: 10)
B. Peptide-heavy chain-GFTFNIY (SEQ ID NO: 11)
(CDR1-Chothia Method), RSKSNNYA
```

-continued (CDR2-Chothia Method), and HGNYYFDY (SEQ ID NO: 12) (CDR3-Chothia Method);

C. Peptide-heavy chain-IYAMN (SEQ ID NO: 13)

(CDR1-Kabat Method), RIRSKSNNYATYYADSMKD (SEQ ID NO: 14)

(CDR2-Kabat Method), and HGNYYFDY (SEQ ID NO: 12) (CDR3-Kabat Method);

D. Nucleic acid-light chain- (SEQ ID NO: 31)
AGTGCCGACTCAAGTGTAAGTTCCAGTTACTTGAAC (CDR1-Chothia and Kabat Methods), (SEQ ID NO: 32)
AGGACATCCAACCTGGCTTCT (CDR2-Chothia and Kabat Methods), and (SEQ ID NO: 33)
CAGCAGTGGAGTGGTTACCCATTCATATTCACG (CDR3-Chothia and Kabat Methods);

E. Nucleic acid-heavy chain-GGATTCACCTTCAATATCTAC (SEQ ID NO: 26)

(CDR1-Chothia Method), AGAAGTAAAAGTAATAATTATGCA (SEQ ID NO: 27)

(CDR2-Chothia Method), and (SEQ ID NO: 28)
CATGGTAACTACTACTTTGACTAC (CDR3-Chothia Method);

F. Nucleic acid-heavy chain-ATCTACGCCATGAAC (SEQ ID NO: 29)

(CDR1-Kabat Method), CGCATAAGAAGTAAAAGTAATAATTATGC (SEQ ID NO: 30)
AACATATTATGCCGATTCAATGAAAGAC (CDR2-Kabat Method), and CATGGTAACTACTAC TTTGACTAC (SEQ ID NO: 28)
(CDR3-Kabat Method);

A. Peptide-light chain-RSSQSLVHSNGNTYLH (SEQ ID NO: 23)

(CDR1-Chothia and Kabat Methods), KVSNRFS (SEQ ID NO: 24)

(CDR2-Chothia and Kabat Methods), and SQSTHVPLT (SEQ ID NO: 25)

(CDR3-Chothia and Kabat Methods);

B. Peptide-heavy chain-GFTFSSF (SEQ ID NO: 18)

(CDR1-Chothia Method), SSGSST (SEQ ID NO: 19)

(CDR2-Chothia Method), and NQSPTGFAY (SEQ ID NO: 20)

(CDR3-Chothia Method);

C. Peptide-heavy chain-SFGMH Method), (SEQ ID NO: 21)

(CDR1-Kabat Method), YISSGSSTIYYADTVKG (SEQ ID NO: 22)

(CDR2-Kabat Method), and NQSPTGFAY (SEQ ID NO: 20)

(CDR3-Kabat Method);

D. Nucleic acid-light chain- (SEQ ID NO: 39)
AGATCTAGTCAGAGCCTTGTACACAGTAATGGAAACACCTATTTACAT (CDR1-Chothia and Kabat Methods), (SEQ ID NO: 40)
AAAGTTTCCAACCGATTTTCT (CDR2-Chothia and Kabat Methods), and (SEQ ID NO: 41)
TCTCAAAGTACACATGTTCCTCTCACG (CDR3-Chothia and Kabat Methods);

E. Nucleic acids-heavy chain-GGATTCACTTTCAGTAGCTTT (SEQ ID NO: 34)

(CDR1-Chothia Method), AGTAGTGGCAGTAGTACC (SEQ ID NO: 35)

(CDR2-Chothia Method), and (SEQ ID NO: 36)
AACCAATCCCCTACGGGGTTTGCTTAC (CDR3-Chothia Method);

F. Nucleic acids-heavy chain-AGCTTTGGAATGCAC (SEQ ID NO: 37)

(CDR1-Kabat Method), (SEQ ID NO: 38)
TACATTAGTAGTGGCAGTAGTACCATCTACTATGCAGACACAGTGAAG
GGC (CDR2-Kabat Method), and (SEQ ID NO: 36)
AACCAATCCCCTACGGGGTTTGCTTAC (CDR3-Kabat Method).

Another embodiment of the invention relates to a hybridoma which produces any such anti-tau antibody disclosed herein, including but not limited to hybridoma h1A6, which produces mAb 1A6 and hybridoma h4G11, which produces mAb 4G11. As used herein, the terms "h1A6" and "h4G11" refer to hybridomas which produce the mAbs 1A6 and 4G11, respectively, and were deposited with the American Type Culture Collection (ATCC, Manassas, Va.) on Feb. 24, 2015. Another embodiment of the invention relates to a human monoclonal antibody, a humanized antibody, a chimeric antibody, affinity matured antibody, mutated antibody or any such antibody as known in the art which comprises the variable light chain, the variable heavy chain, or both the variable light chain and variable heavy chain of the 4G11 mAb (as secreted from h4G11), including but not limited to the entire respective variable light or heavy chain, a fragment thereof or a substantially homologous fragment thereof from 4G11, any such fragment or substantially homologous fragment including but not limited to one, two, three, four, five or all six CDRs (as determined by either the Kabat and/or Chothia methodology, as described herein, as for example each of three CDRs from the variable light chain and/or each of three CDRs from the variable heavy chain)

from the variable light chain and/or the variable heavy chain of the monoclonal antibody 4G11. An additional embodiment of the invention relates to a human monoclonal antibody, a humanized antibody, a chimeric antibody, affinity matured antibody, mutated antibody or any such antibody as known in the art which comprises the variable light chain, the variable heavy chain, or both the variable light chain and variable heavy chain of the 1A6 mAb (as secreted from h1A6), including but not limited to the entire respective variable light or heavy chain, a fragment thereof or a substantially homologous fragment thereof from 1A6, any such fragment or substantially homologous fragment including but not limited to one, two, three, four, five or all six CDRs (as determined by either the Kabat and/or Chothia methodology, as described herein, as for example each of three CDRs from the variable light chain and/or each of three CDRs from the variable heavy chain) from the variable light chain and/or the variable heavy chain of the monoclonal antibody 1A6. Again, any such fragments may include one or a portion of the variable light and heavy chain sequences or CDR regions of 4G11 and/or 1A6, or may be substantially homologous to such sequences. Again, any such antibody may take the form of a human monoclonal antibody, a humanized antibody, a chimeric antibody, an affinity matured antibody, a mutated antibody or any such antibody generated by methodology as known in the art associated with improving the efficacy and/or safety of any such antibody, especially as related to administration to humans.

In certain aspects, the antibodies or portion of the anti-tau antibodies of the present invention are encoded in an isolated nucleic acid molecule, which includes (or encodes) one or more of the foregoing sequences, fragments, or homologues thereof. The nucleic acid molecule may encode the variable heavy chain and/or light chain and/or CDRs, including fragments thereof, of monoclonal antibodies 4G11 and 1A6. Such nucleic acid sequences may be cloned into an expression vector and inserted into a recombinant host cell. To this end, the present invention includes each of the isolated nucleic acids, the recombinant expression vectors encoding such isolated nucleic acids and host cell expressing such vectors.

Anti-tau antibodies of the present invention that incorporate one or more of the foregoing sequences, including substantially homologous variants thereof, may be provided as monoclonal antibodies, chimeric antibodies, humanized antibodies, human monoclonal antibodies, affinity matured antibodies, mutated antibodies or other antibody variants known in the art.

The present invention also relates to treatment methods using one or a combination of the anti-tau antibodies of the present invention alone or in a pharmaceutical composition. One embodiment of a treatment method includes treating, preventing, or reducing one or more symptoms associated with a neurodegenerative tauopathy disease state, as defined herein, by administering to the mammal an effective amount of at least one anti-tau antibody of the present invention. In further embodiments, the treatment methods of the present invention include modulation of tau aggregation in the subject. In certain aspects, the present invention includes the preparation of a pharmaceutical or diagnostic composition for prophylactic and therapeutic treatment of a tauopathic disease, monitoring the progression of a tauopathic disease or a response to a tauopathic disease treatment in a subject or for determining a subject's risk for developing a tauopathic disease.

Additionally, the present invention includes diagnostic assays, drug screening assays, and the like for diagnosing in a bodily fluid of a patient or subject the presence of a tau protein, or an aggregation of tau proteins, or for identifying therapeutics capable of treating taupathic diseases. Anti-tau antibodies of the present invention may also be used as a molecular tool to study the activity of tau in a tau expressing cell and/or the impact of tau aggregation to the cell, central nervous system, and subject.

In conjunction with such embodiments, the present invention also includes a kit for detecting tau protein that includes (1) an antibody or a fragment thereof, capable of specifically binding in vitro to an epitope of a tau protein; and, (2) a reagent that binds, directly, or indirectly, to said antibody or the fragment thereof.

One of skill in the art will readily appreciate that the foregoing is not necessarily limiting to the invention and that additional embodiments and advantages of the present invention are readily available based on the disclosure provided herein.

To aid in the understanding of the invention, the following non-limiting definitions are provided:

As used herein, the term "epitope" refers to a site on an antigen to which B and/or T cells respond or a site on a molecule against which an antibody can or will be produced and/or to which an antibody can or will bind. For example, an epitope can be recognized by an antibody defining the epitope. An epitope can be either a "linear epitope" (where a primary amino acid primary sequence comprises the epitope; typically at least 3 contiguous amino acid residues, and more usually, at least 5, and up to about 8 to about 10 amino acids in a unique sequence) or a "conformational epitope" (an epitope wherein the primary, contiguous amino acid sequence is not the sole defining component of the epitope). A conformational epitope may comprise an increased number of amino acids relative to a linear epitope, as this conformational epitope recognizes a three-dimensional structure of the peptide or protein. For example, when a protein molecule folds to form a three dimensional structure, certain amino acids and/or the polypeptide backbone forming the conformational epitope become juxtaposed enabling the antibody to recognize the epitope. Methods of determining conformation of epitopes include but are not limited to, for example, x-ray crystallography, two-dimensional nuclear magnetic resonance spectroscopy and site-directed spin labeling and electron paramagnetic resonance spectroscopy. See, for example, Epitope Mapping Protocols in Methods in Molecular Biology, Vol. 66, Glenn E. Morris, Ed. (1996), the disclosure of which is incorporated in its entirety herein by reference.

As used herein, the terms "isolated" or "purified" are as used within the art, namely the state in which antibodies/specific binding members, nucleic acid molecules and such are found. Antibodies/specific binding members and nucleic acid molecules will be free or substantially free of material with which they are naturally associated such as other polypeptides or nucleic acids with which they are found in their natural environment, or the environment in which they are prepared (e.g. cell culture) when such preparation is by recombinant DNA technology (practiced in vitro) or in vivo. "Isolated" or "purified" covers any form containing the identified and characterized component(s) of the present invention following removal from that initial environment. Examples, but certainly not limitations, include pharmaceutical formulations, formulation with diluents, antibodies/specific binding members, nucleic acid molecules and portions thereof which have been modified (e.g., antibody glycosylation) either in vitro or in vivo and removed from that environment.

The terms "subject" or "patient" is meant to include any member of the Phylum Chordata, including, without limitation, humans and other primates, including nonhuman primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like.

The term "treating" or "treatment" of a disease refers to executing a protocol, which may include administering one or more drugs to a subject (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" or "reducing" signs or symptoms of disease. In addition, "treating" or "treatment" does not require complete alleviation of signs or symptoms, does not require a cure, and specifically includes protocols which have only a marginal positive effect on the subject.

As used herein, the terms "effective amount" or "pharmaceutically effective amount," as provided herein, refers to a nontoxic but sufficient amount of the active ingredient in order to provide the desired biological result. An appropriate "effective" amount in any individual case may be determined by one of ordinary skill in the art using routine experimentation.

As used herein, the terms "pharmaceutically acceptable" or "pharmacologically acceptable" mean a material may be administered to an individual in a drug delivery device along with the formulated biological agent without causing any undesirable biological effects or interacting in a deleterious manner with any of the components of the composition in which it is contained (e.g., a "pharmaceutically acceptable composition").

As used herein, the phrases "physiologically acceptable carrier" and "pharmaceutically acceptable carrier" which may be interchangeably used refer to a carrier, diluent, and excipient that does not cause significant irritation to an organism and does not abrogate the biological activity and properties of the administered compound. An adjuvant is included under these phrases.

As used herein, the term "excipient" refers to an inert substance added to a pharmaceutical composition to further facilitate administration of an active ingredient.

By "specifically binding" or "binding affinity," it is generally meant that a binding molecule, e.g., an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. A skilled artisan understands that an antibody can specifically bind to, or specifically recognize an isolated polypeptide comprising, or consisting of, amino acid residues corresponding to a linear portion of a noncontiguous epitope. The term "specificity" is used herein to qualify the relative affinity by which a certain antibody binds to a certain epitope. For example, antibody "A" can be deemed to have a higher specificity for a given epitope than antibody "B," or antibody "A" can be said to bind to epitope "C" with a higher specificity than it has for related epitope "D."

As used herein, the term "affinity" refers to a measure of the strength of the binding of an individual epitope with the CDR of a binding molecule, e.g., an immunoglobulin molecule; see, e.g., Harlow et al, Antibodies: A Laboratory Manual, Cold Spring Harbor Laboratory Press, 2nd ed. (1988) at pages 27-28. The affinity of an antibody for an antigen can be determined experimentally using any suitable method; see, for example, Berzofsky et al, "Antibody-Antigen Interactions" In Fundamental Immunology, Paul, W. E., Ed., Raven Press New York, N.Y. (1984), Kuby, Janis Immunology, W. H. Freeman and Company New York, N.Y. (1992), and methods described herein. General techniques for measuring the affinity of an antibody for an antigen include ELISA, RIA, and surface plasmon resonance. The measured affinity of a particular antibody-antigen interaction can vary if measured under different conditions, e.g., salt concentration, pH. Thus, measurements of affinity and other antigen-binding parameters, e.g., $\frac{3}{4}$, $IC_{50}$, are preferably made with standardized solutions of antibody and antigen, and a standardized buffer.

As used herein, "conservatively modified variants" or "conservative amino acid substitution" or the like refers to substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., Molecular Biology of the Gene, The Benjamin/Cummings Pub. Co., p. 224 (4th Edition 1987)). Such exemplary substitutions are preferably made in accordance with those set forth below as follows: (original residue)/[conservative substitution]: (Ala)/[Gly, Ser]; (Arg)/[Lys, His](Asn)/[Gln, His]; (Asp)/[Glu, Asn]; (Cys)/[Ser, Ala]; (Gln)/[Asn]; (Glu)/[Asp, Gln]; (Gly)/[Ala]; (His)/[Asn, Gln]; (Ile)/[Leu, Val]; (Leu)/[Ile, Val]; (Lys)/[Arg, His]; (Met)/[Leu, Ile, Tyr]; (Phe)/[Tyr, Met, Leu]; (Pro)/[Ala]; (Ser)/[Thr]; (Thr)/[Ser]; (Trp)/[Tyr, Phe]; (Tyr)/[Trp, Phe]; (Val)/[Ile, Leu].

BRIEF DESCRIPTION OF THE FIGURES

FIGS. 2A and 2B illustrate Western blot analysis of 4G11 (IgA) (FIG. 2A) and 1A6 (IgM) (FIG. 2B), respectively. Each of the lanes are labeled with the Tau isoform (i.e, 352, 381, 383, 410, 412 and/or 441).

FIG. 5 illustrates the amino acid sequence of the Tau 441 protein (presented as SEQ ID NO: 6) and labels each of the N-terminus binding domains (N1—shaded & N2—underlined) and C-terminus binding domains (R1, R2, & R3—shaded & R4—underlined).

DETAILED DESCRIPTION

Figure 1:
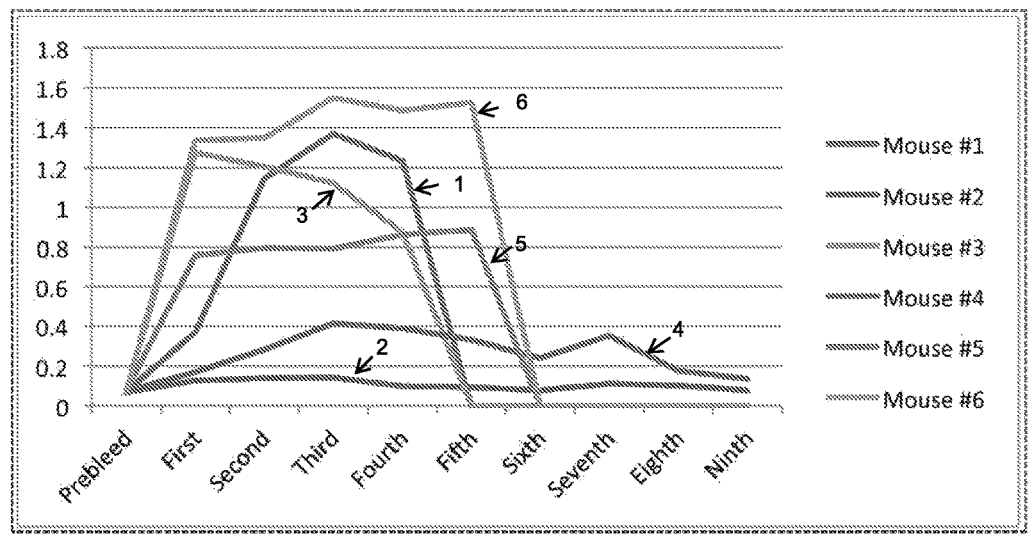
FIG. 1 provides a graphic illustration of the ELISA results from serum samples obtained from 6 mice inoculated with the tau protein, and as discussed in Example 1.

Tau protein aggregation and the formation of neurofibrillary tangles is thought to be a molecular hallmark for Alzheimer's Disease (AD), among other neurodegenerative taupathies. Accordingly, it presents a viable target for the study of such taupathies (particularly AD) or, alternatively, for a method of diagnosing, monitoring, studying, and/or treating a patient diagnosed with a neurodegenerative taupathy (such as AD).

In certain non-limiting aspects, the present invention relates to isolated antibodies that specifically interact with and show measurable affinity to one or more epitopes of one or more tau protein isoforms, referred to herein at "anti-tau antibodies." Such antibodies may be used for the identification of and/or modulation of tau protein activity or aggregation, to study its effects on cell function and, in certain embodiments, for the treatment, prevention, diagnosis, and/or monitoring of a disease or condition associated with the tau protein expression or aggregation. In certain embodiments, the anti-tau antibodies may be administered to a subject to treat or prevent a neurodegenerative tauopathy, including AD, and/or for preventing the formation of neurofibrillary tangles by the tau protein, which is a symptom of the disease. In certain embodiments, the anti-tau antibodies may be used to diagnosis and/or monitor a neurodegenerative tauopathy (such as AD) by monitoring the formation and concentration of neurofibrillary tangles in a patient.

As used herein, the terms "tau proteins" or "tau protein isoforms" refer to any form of the tau protein, but in certain aspects the forms of tau protein expressed in the human brain. In certain aspects, it refers to one of the following isoforms of the human form of the protein, which has the following amino acid sequences:

```
Tau Isoform 352
                                          (SEQ ID NO: 1)
MAEPRQEFEVMEDHAGTYGLGDRKDQGGYTMHQDQEGDTDAGLKAEEAGI

GDTPSLEDEAAGHVTQARMVSKSKDGTSDDKKAKGADGKTKIATPRGAA

PPGQKGQANATRIPAKTPPAPKTPPSSGEPPKSGDRSGYSSPGSPGTPGS

RSRTPSLPTPPTREPKKVAVVRTPPKSPSSAKSRLQTAPVPMPDLKNVKS

KIGSTENLKHQPGGGKVQIVYKPVDLSKVTSKCGSLGNIHHKPGGGQVEV

KSEKLDFKDRVQSKIGSLDNITHVPGGGNKKIETHKLTFRENAKAKTDHG

AEIVYKSPVVSGDTSPRHLSNVSSTGSIDMVDSPQLATLADEVSASLAKQ

GL;

Tau Isoform 383
                                          (SEQ ID NO: 2)
MAEPRQEFEVMEDHAGTYGLGDRKDQGGYTMHQDQEGDTDAGLKAEEAGI

GDTPSLEDEAAGHVTQARMVSKSKDGTGSDDKKAKGADGKTKIATPRGAA

PPGQKGQANATRIPAKTPPAPKTPPSSGEPPKSGDRSGYSSPGSPGTPGS

RSRTPSLPTPPTREPKKVAVVRTPPKSPSSAKSRLQTAPVPMPDLKNVKS

KIGSTENLKHQPGGGKVQIINKKLDLSNVQSKCGSKDNIKHVPGGGSVQI

VYKPVDLSKVTSKCGSLGNIHHKPGGGQVEVKSEKLDFKDRVQSKIGSLD

NITHVPGGGNKKIETHKLTFRENAKAKTDHGAEIVYKSPVVSGDTSPRHL

SNVSSTGSIDMVDSPQLATLADEVSASLAKQGL;

Tau Isoform 381
                                          (SEQ ID NO: 3)
MAEPRQEFEVMEDHAGTYGLGDRKDQGGYTMHQDQEGDTDAGLKESPLQT

PTEDGSEEPGSETSDAKSTPTAEAEEAGIDTPSLEDEAAGHVTQARMVS

KSKDGTGSDDKKAKGADGKTKIATPRGAAPPGQKGQANATRIPAKTPPAP

KTPPSSGEPPKSGDRSGYSSPGSPGTPGSRSRTPSLPTPPTREPKKVAVV

RTPPKSPSSAKSRLQTAPVPMPDLKNVKSKIGSTENLKHQPGGGKVQIVY

KPVDLSKVTSKCGSLGNIHHKPGGGQVEVKSEKLDFKDRVQSKIGSLDNI

THVPGGGNKKIETHKLTFRENAKAKTDHGAEIVYKSPVVSGDTSPRHLSN

VSSTGSIDMVDSPQLATLADEVSASLAKQGL;

Tau Isoform 412
                                          (SEQ ID NO: 4)
MAEPRQEFEVMEDHAGTYGLGDRKDQGGYTMHQDQEGDTDAGLKESPLQT

PTEDGSEEPGSETSDAKSTPTAEAEEAGIDTPSLEDEAAGHVTQARMVS

KSKDGTGSDDKKAKGADGKTKIATPRGAAPPGQKGQANATRIPAKTPPAP

KTPPSSGEPPKSGDRSGYSSPGSPGTPGSRSRTPSLPTPPTREPKKVAVV

RTPPKSPSSAKSRLQTAPVPMPDLKNVKSKIGSTENLKHQPGGGKVQIIN

KKLDLSNVQSKCGSKDNIKHVPGGGSVQIVYKPVDLSKVTSKCGSLGNIH

HKPGGGQVEVKSEKLDFKDRVQSKIGSLDNITHVPGGGNKKIETHKLTFR

ENAKAKTDHGAEIVYKSPVVSGDTSPRHLSNVSSTGSIDMVDSPQLATLA

DEVSASLAKQGL;

Tau Isoform 410
                                          (SEQ ID NO: 5)
MAEPRQEFEVMEDHAGTYGLGDRKDQGGYTMHQDQEGDTDAGLKESPLQT

PTEDGSEEPGSETSDAKSTPTAEDVTAPLVDEGAPGKQAAAQPHTEIPEG

TTAEEAGIGDTPSLEDEAAGHVTQARMVSKSKDGTGSDDKKAKGADGKTK

IATPRGAAPPGQKGQANATRIPAKTPPAPKTPPSSGEPPKSGDRSGYSSP

GSPGTPGSRSRTPSLPTPPTREPKKVAVVRTPPKSPSSAKSRLQTAPVPM

PDLKNVKSKIGSTENLKHQPGGGKVQIVYKPVDLSKVTSKCGSLGNIHHK

PGGGQVEVKSEKLDFKDRVQSKIGSLDNITHVPGGGNKKIETHKLTFREN
```

-continued

AKAKTDHGAEIVYKSPVVSGDTSPRHLSNVSSTGSIDMVDSPQLATLADE

VSASLAKQGL;

Tau Isoform 441

(SEQ ID NO: 6)
MAEPRQEFEVMEDHAGTYGLGDRKDQGGYTMHQDQEGDTDAGLKESPLQT

PTEDGSEEPGSETSDAKSTPTAEDVTAPLVDEGAPGKQAAAQPHTEIPEG

TTAEEAGIGDTPSLEDEAAGHVTQARMVSKSKDGTGSDDKKAKGADGKTK

IATPRGAAPPGQKGQANATRIPAKTPPAPKTPPSSGEPPKSGDRSGYSSP

GSPGTPGSRSRTPSLPTPPTREPKKVAVVRTPPKSPSSAKSRLQTAPVPM

PDLKNVKSKIGSTENLKHQPGGGKVQIINKKLDLSNVQSKCGSKDNIKHV

PGGGSVQIVYKPVDLSKVTSKCGSLGNIHHKPGGGQVEVKSEKLDFKDRV

QSKIGSLDNITHVPGGGNKKIETHKLTFRENAKAKTDHGAEIVYKSPVVS

GDTSPRHLSNVSSTGSIDMVDSPQLATLADEVSASLAKQGL.

The present invention, however, is not limited to these forms and may include any variant, natural or synthetic, or mutated sequence that exhibits the properties of a tau protein (including aggregation) in or around a targeted cell or cell population that are discussed herein or otherwise known in the art, including those found in humans or other mammalian species.

The targeted epitope(s) of the anti-tau antibodies include any one or more peptide sequences of a tau isoform against which one or more antibodies of the present invention will bind with specific or measurable affinity. Such sequences may include active or non-active regions of the protein and include either linear epitopes and/or conformation epitopes, as defined herein. In certain aspects, they include one or more regions where the binding of the antibodies results in a measurable reduction of the tau protein aggregation in the host cell. To this end, in certain aspects, the epitope is at a position of the protein where the binding of the antibody modifies protein activity, and in certain aspects self-assembly or aggregation into neurofibrillary tangles, such as active site blocking, steric hindrance, allosteric inhibition, or the like. Such a binding site may include, but is not limited to, one or more epitopes within or near a tau protein binding domain.

In certain non-limiting embodiments, the epitope is provided at a residue within the $NH_2$-terminus binding domain of the tau isoform. In certain embodiments, the epitope is a linear epitope having the sequence EEPGSETS (SEQ ID NO: 7), which resides at residues 57-64 of the tau 381, 410, 412, and 441 isoforms.

In further embodiments, the epitope is a linear epitope having the sequence EFEVMEDHAGT (SEQ ID NO: 8), which resides at residues 7-18 of the tau 352, 381, 383, 410, 412, and 441 isoforms. In even further embodiments, the epitope is conformational and includes an epitope having the sequence EFEVMEDHAGT (SEQ ID NO: 8) and a second epitope having the sequence LPTPPT (SEQ ID NO: 9), which resides at residues 158-162 of the tau 352 and 383 isoforms, residues 187-191 of the tau 381 and 412 isoforms; and residues 216-220 of the tau 410 and 441 isoforms.

The epitopes of the present invention are not limited to the exact sequences within SEQ ID NOs: 7-9 and may include any sequence having at least 70% homology, 80% homology, 90% homology or 99% homology.

The anti-tau antibodies of the present invention include two identical heavy chains and two light chains containing one or more of the antigen binding domains identified herein. The light chain includes one variable domain ($V_L$) and one constant domain ($C_L$). The heavy chain also includes one variable domain ($V_H$) and, depending on the class or isotype of antibody, three or four constant domains ($C_{H1}$, $C_{H2}$, $C_{H3}$ and $C_{H4}$). Isotypes include, but are not limited to, IgA, IgD, IgE, IgG, and IgM, with IgA and IgG further subdivided into subclasses or subtypes. In certain non-limiting inventions, the isotype of the present invention is IgG, which includes one or a combination of its sub-types (e.g., IgG1, IgG2, IgG3, and IgG4). In further non-limiting embodiments, the isotype of the present invention is IgA, including the 4G11 antibody and including one or a combination of its sub-types or isoforms (e.g., IgA1 and IgA2). In even further non-limiting embodiments, the isotype of the present invention is IgM, including the 1A6 antibody.

The paired heavy chain constant domains are generally understood to define the Fc region of the antibody. Based on its sequence, it provides the antibody with one or more of the isotypes discussed above. The Fc region is associated with Fc receptor binding, activation of complement-mediated cytotoxicity and antibody-dependent cellular-cytotoxicity. To this end, it is at least partially responsible for eliciting immunological reactivity.

The $V_L$ and $V_H$ domains of the antibody are generally defined as the "Fv" region and constitute the antigen-binding site. A single chain Fv (scFv) includes a protein containing a $V_L$ domain and a $V_H$ domain on one polypeptide chain, wherein the N terminus of one domain and the C terminus of the other domain are joined by a flexible linker. A "Fab" region refers to the portion of the antibody including the $V_L$-$C_L$ (i.e, a light chain) and $V_H$-$C_H$ (also designated "Fd").

Present within each $V_L$ and $V_H$ domain of the Fv region of the antibody are eight framework regions (FR) and six total complementarity-determining regions (CDRs). Four FRs and three CDRs are found in each $V_L$ chain and the $V_H$ chain. The four FR regions (FR1, FR2, FR3, and FR4) are relatively conserved, while the CDR regions (CDR1, CDR2, and CDR3) represent the hyper-variable portion of the antibody primarily responsible for the recognition and binding of the targeted epitope sequence. Typically, the FR and CDRs regions are arranged from $NH_2$ terminus to the COOH terminus of the antibody as follows: FR1, CDR1, FR2, CDR2, FR3, CDR3, FR4.

One embodiment of the present invention relates the isolated or purified monoclonal antibody 4G11.

Another embodiment of the present invention relates to the isolated or purified monoclonal antibody 1A6.

An additional embodiment as disclosed herein related to antibodies that represent variants of the monoclonal antibodies 4G11 and/or 1A6, i.e antibodies having one or a combination of peptide sequences from the antibodies 4G11 and/or 1A6. To this end, with any of the above embodiments, the variant of the antibody or antibody fragment of the invention may comprise one, two or three conservatively modified amino acid substitutions. In any of the above embodiments, the antibody or antibody fragment of the invention may comprise a human heavy chain constant region or a variant thereof, wherein the variant comprises up to 20 conservatively modified amino acid substitutions; and/or a human light chain constant region or a variant thereof, wherein the variant comprises up to 20 conservatively modified amino acid substitutions. In some embodiments, the variant may comprise up to 10 conservatively modified amino acid substitutions. In some embodiments, the variant may comprise up to 5 conservatively modified amino acid substitutions. In some embodiments, the variant may comprise up to 3 conservatively modified amino acid substitutions. In any of the above embodiments, the human heavy chain constant region or variant thereof may be, but is in no way limited to, the IgG isotype (e.g., IgG1, IgG2, IgG3, and IgG4 sub-types), IgA isotype (e.g., IgA1, IgA2 subtypes), IgD isotype, IgE isotype, or IgM isotype.

Embodiments of the invention include the entire antibody, a fragment or substantially homologous fragment of the monoclonal antibody 4G11. Any such entire antibody, fragment of substantially homologous fragment (such as, but not limited to, a substantially homologous fragment containing one or more conservative amino acid substitutions) being derived from the 4G11 antibody, and any such fragment or substantially homologous fragment including but not limited to one, two, three, four, five or all six CDRs (as determined by either the Kabat and/or Chothia methodology, as described herein, as for example each of three CDRs from the variable light chain and/or each of three CDRs from the variable heavy chain) from the variable light chain and/or the variable heavy chain of the monoclonal antibody 4G11. Additional embodiments include the entire antibody, a fragment or substantially homologous fragment of the monoclonal antibody 1A6, with any such entire antibody, fragment or substantially homologous fragment (such as, but not limited to, a substantially homologous fragment containing one or more conservative amino acid substitutions) being derived from the 1A6 antibody, and any such fragment or substantially homologous fragment including but not limited to one, two, three, four, five or all six CDRs (as determined by either the Kabat and/or Chothia methodology, as described herein, as for example each of three CDRs from the variable light chain and/or each of three CDRs from the variable heavy chain) from the variable light chain and/or the variable heavy chain of the monoclonal antibody 1A6. Fragments may include, but are not limited to, one or a portion of the variable light and/or heavy chain sequences or CDR regions of 4G11 and/or 1A6, or may be substantially homologous to such sequences. Again, any such antibody may take the form of a human monoclonal antibody, a humanized antibody, a chimeric antibody, affinity matured antibody, mutated antibody or any such antibody generated by methodology as known in the art.

Another embodiment of the invention relates to a human monoclonal antibody, a humanized antibody, a chimeric antibody, affinity matured antibody, mutated antibody or any such antibody generated by methodology as known in the art which comprises the variable light chain, the variable heavy chain, or both the variable light chain and variable heavy chain of the 4G11 mAb (as secreted from h4G11), including but not limited to the entire respective variable light or heavy chain, a fragment thereof or a substantially homologous fragment thereof from 4G11, and any such fragment or substantially homologous fragment including but not limited to one, two, three, four, five or all six CDRs (as determined by either the Kabat and/or Chothia methodology, as described herein, as for example each of three CDRs from the variable light chain and/or each of three CDRs from the variable heavy chain) from the variable light chain and/or the variable heavy chain of the monoclonal antibody 4G11. An additional embodiment of the invention relates to a human monoclonal antibody, a humanized antibody, a chimeric antibody, affinity matured antibody, mutated antibody or any such antibody generated by methodology as known in the art which comprises the variable light chain, the variable heavy chain, or both the variable light chain and variable heavy chain of the 1A6 mAb (as secreted from h1A6), including but not limited to the entire respective variable light or heavy chain, a fragment thereof or a substantially homologous fragment thereof from 1A6. and any such fragment or substantially homologous fragment including but not limited to one, two, three, four, five or all six CDRs (as determined by either the Kabat and/or Chothia methodology, as described herein, as for example each of three CDRs from the variable light chain and/or each of three CDRs from the variable heavy chain) from the variable light chain and/or the variable heavy chain of the monoclonal antibody 1A6. Again, any such fragments may include one or a portion of the variable light and heavy chain sequences or CDR regions of 4G11 and/or 1A6, or may be substantially homologous to such sequences. Again, any such antibody may take the form of a human antibody, a humanized antibody, a chimeric antibody, an affinity matured antibody, a mutated antibody, or any such antibody generated by methodology as known in the art.

An additional embodiment of the present invention relates to a hybridoma which produces or secretes an anti-tau antibody as disclosed herein, including but in no way limited to hybridoma h4G11, which secretes 4G11, and hybridoma h1A6, which secretes 1A6; both hybridomas having been deposited with the American Type Culture Collection on Feb. 24, 2015, as described more fully herein.

The following Tables 1 and 2 provide the amino acid sequences of the variable light chain and a variable heavy chains, respectively, of antibodies 4G11 and 1A6:

TABLE 1

Variable Light Chain Sequences

| 4G11 | ENVLTQSPAIMAASLGQKVTMTCSADSSVSSSYLNWYQQKSGASP KPLIHRTSNLASGVPARFSGSGSGTSYSLTISSVEAEDDATYYCQ QWSGYPFIFTFGSGTKLEIK (SEQ ID NO: 44) |
| --- | --- |
| 1A6 | DVVMTQTPLSLPVSLGDQASISCRSSQSLVHSNGNTYLHWYLQKP GQSPKLLIYKVSNRFSGVPDRFSGSGSGTDFTLKISRVEAEDLGV YFCSQSTHVPLTFGAGTKLELK (SEQ ID NO: 48) |

TABLE 2

Variable Heavy Chain Sequences

| 4G11 | EVQLVESGGGLVQPKGSLKLSCAASGFTFNIYAMNWVRQAPGKGL EWVARIRSKSNNYATYYADSMKDRFTISRDDSQSMLYLQMNNLKT EDTAMYYCVRHGNYYFDYWGQGTTLTVSS (SEQ ID NO. 42) |
| --- | --- |
| 1A6 | DVQLVESGGGLVQPGGSRKLSCAASGFTFSSFGMHWVRQVPEKGL EWVAYISSGSSTIYYADTVKGRFTISRDNPKNTLFLQMTSLRSED TAMYYCASNQSPTGFAYWGQGTLVTVSA (SEQ ID NO: 46) |

The following Tables 3-5 provide the amino acid sequences of the variable light chain CDRs and the variable heavy chain CDRs, respectively, of antibodies 4G11 and 1A6. Table 3 provides the variable light chain CDR sequences according to both the Chothia and Kabat Method. Table 4 provides the variable heavy chain CDR sequences according to the Chothia Method. See Chothia et al., "Canonical structures for the hypervariable regions of immunoglobulins," J. Mol. Biol. 1987, Aug. 20; 196(4): 901-917, the contents of which are incorporated by reference herein in its entirety. Table 5 provides the variable heavy chain CDR sequences according to the Kabat Method. See Kabat et al., "Sequences of Proteins of Immunological Interest," U.S. Department of Health and Human Services, 1983, the contents of which are incorporated by reference herein in its entirety.

TABLE 3

Variable Light Chain CDR Sequences - Chothia & Kabat Method

| | CDR1 | CDR2 | CDR3 |
|---|---|---|---|
| 4G11 | SADSSVSSSYLN (SEQ ID. NO.: 15) | RTSNLAS (SEQ ID. NO.: 16) | QQWSGYPFIFT (SEQ ID. NO.: 17) |
| 1A6 | RSSQSLVHSNGNTYLH (SEQ ID. NO.: 23) | KVSNRFS (SEQ ID. NO.: 24) | SQSTHVPLT (SEQ ID. NO.: 25) |

TABLE 4

Variable Heavy Chain CDR Sequences - Chothia Method

| | CDR1 | CDR2 | CDR3 |
|---|---|---|---|
| 4G11 | GFTFNIY (SEQ ID. NO.: 10) | RSKSNNYA (SEQ ID. NO.: 11) | HGNYYFDY (SEQ ID. NO.: 12) |
| 1A6 | GFTFSSF (SEQ ID. NO.: 18) | SSGSST (SEQ ID. NO.: 19) | NQSPTGFAY (SEQ ID. NO.: 20) |

TABLE 5

Variable Heavy Chain CDR Sequences - Kabat Method

| | CDR1 | CDR2 | CDR3 |
|---|---|---|---|
| 4G11 | IYAMN (SEQ ID. NO.: 13) | RIRSKSNNYATYYADSMKD (SEQ ID. NO.: 14) | HGNYYFDY (SEQ ID. NO.: 12) |
| 1A6 | SFGMH (SEQ ID. NO.: 21) | YISSGSSTIYYADTVKG (SEQ ID. NO.: 22) | NQSPTGFAY (SEQ ID. NO.: 20) |

As discussed herein, the anti-tau antibodies of the present invention, may include the foregoing variable light chain, variable heavy chain, and/or CDR peptide sequences exactly or may be sufficiently homologous or substantially the same as one of the foregoing sequences, so as to exhibit specific or measurable binding affinity to the tau protein, including to one or more of the epitopes identified herein. Substantially the same amino acid sequence or sufficiently homologous is defined herein as a sequence with at least 70%, at least about 80%, at least about 90%, at least about 95% or at least about 99% homology or identity to a compared amino acid sequence, as determined by the FASTA search method in accordance with Pearson and Lipman, Proc. Natl. Acad. Sci. USA 85:2444-2448 (1988), the contents of which are incorporated herein by reference. Anti-tau antibodies of the present invention may be provided as naturally occurring antibodies, bivalent fragments such as (Fab')$_2$, monovalent fragments such as Fab, single chain antibodies, single chain Fv (scFv), single domain antibodies, multivalent single chain antibodies, diabodies, triabodies, and the like that bind with measurable affinity to the targeted antigen or epitopes.

Also included within the present invention are the isolated nucleic acid molecules encoding the amino acid sequences (or fragments thereof) above, which may include the $V_H$ and/or $V_L$ regions and/or CDRs of 4G11 and/or 1A6 antibodies. The Variable Light and Heavy Chain DNA sequences for 4G11 and 1A6 are as follows in Tables 6 and 7.

TABLE 6

Variable Light Chain DNA Sequences

4G11 GAAAATGTGCTCACCCAGTCTCCAGCAATAATGGCTGCCTCTCTG
GGGCAGAAGGTCACCATGACCTGCAGTGCCGACTCAAGTGTAAGT
TCCAGTTACTTGAACTGGTACCAGCAGAAGTCAGGCGCTTCCCCC
AAACCCTTGATTCATAGGACATCCAACCTGGCTTCTGGAGTCCCA
GCTCGCTTCAGTGGCAGTGGGTCTGGGACCTCTTACTCTCTCACA
ATCAGCAGCGTGGAGGCTGAAGATGATGCAACTTATTACTGCCAG
CAGTGGAGTGGTTACCCATTCATATTCACGTTCGGCTCGGGGACA
AAGTTGGAAATAAAA (SEQ ID NO: 45)

1A6 GATGTTGTGATGACCCAAACTCCACTCTCCCTGCCTGTCAGTCTT
GGAGATCAAGCCTCCATCTCTTGCAGATCTAGTCAGAGCCTTGTA
CACAGTAATGGAAACACCTATTTACATTGGTACCTGCAGAAGCCA
GGCCAGTCTCCAAAGCTCCTAATCTACAAAGTTTCCAACCGATTT
TCTGGGGTCCCAGACAGGTTCAGTGGCAGTGGATCAGGGACAGAT
TTCACACTCAAGATCAGCAGAGTGGAGGCTGAGGATCTGGGAGTT
TATTTCTGCTCTCAAAGTACACATGTTCCTCTCACGTTCGGTGCT
GGGACCAAGCTGGAGCTGAAA (SEQ ID NO: 49)

TABLE 7

Variable Heavy Chain DNA Sequences

4G11 GAGGTGCAGCTTGTTGAGTCTGGTGGAGGATTGGTGCAGCCTAAA
GGGTCATTGAAACTCTCATGTGCAGCCTCTGGATTCACCTTCAAT
ATCTACGCCATGAACTGGGTCCGCCAGGCTCCAGGAAAGGGTTTG
GAATGGGTTGCTCGCATAAGAAGTAAAAGTAATAATTATGCAACA
TATTATGCCGATTCAATGAAAGACAGGTTCACCATCTCCAGAGAT
GATTCACAAAGCATGCTCTATCTGCAAATGAACAACTTGAAAACT
GAGGACACAGCCATGTATTACTGTGTGAGACATGGTAACTACTAC
TTTGACTACTGGGGCCAAGGCACCACTCTCACAGTCTCCTCA
(SEQ ID NO: 43)

1A6 GATGTGCAGCTGGTGGAGTCTGGGGGAGGCTTAGTGCAGCCTGGA
GGGTCCCGGAAACTCTCCTGTGCAGCCTCTGGATTCACTTTCAGT
AGCTTTGGAATGCACTGGGTTCGTCAGGTTCCAGAGAAGGGGCTG
GAGTGGGTCGCATACATTAGTAGTGGCAGTAGTACCATCTACTAT
GCAGACACAGTGAAGGGCCGATTCACCATCTCCAGAGACAATCCC
AAGAACACCCTGTTCCTGCAAATGACCAGTCTAAGGTCTGAGGAC
ACGGCCATGTATTACTGTGCAAGTAACCAATCCCCTACGGGGTTT
GCTTACTGGGGCCAAGGGACTCTGGTCACTGTCTCTGCA
(SEQ ID. NO.: 47)

The DNA sequences for the Variable Light and Heavy Chain CDR sequences of 4G11 and 1A6 are as follows in Tables 8-10. Table 8 provides the variable light chain CDR sequences according to both the Chothia and Kabat Method. Table 9 provides the variable heavy chain CDR sequences according to the Chothia Method, defined above. Table 10 provides the variable heavy chain CDR sequences according to the Kabat Method, defined above.

TABLE 8

Variable Light Chain CDR Sequences - Chothia & Kabat

| | CDR1 | CDR2 | CDR3 |
|---|---|---|---|
| 4G11 | AGTGCCGACTCAAGTGTAA GTTCCAGTTACTTGAAC (SEQ ID NO: 31) | AGGACATCCAA CCTGGCTTCT (SEQ ID NO: 32) | CAGCAGTGGAGTGGTTA CCCATTCATATTCACG (SEQ ID NO: 33) |

TABLE 8-continued

Variable Light Chain CDR Sequences - Chothia & Kabat

| | CDR1 | CDR2 | CDR3 |
|---|---|---|---|
| 1A6 | AGATCTAGTCAGAGCCTTG TACACAGTAATGGAAA CACCTATTTACAT (SEQ ID NO: 39) | AAAGTTTCCAA CCGA TTTTCT (SEQ ID NO: 40) | TCTCAAAGTACA CATGTTCCTCTC ACG (SEQ ID NO: 41) |

TABLE 9

Variable Heavy Chain CDR Sequences - Chothia

| | CDR1 | CDR2 | CDR3 |
|---|---|---|---|
| 4G11 | GGATTCACCTTCAATA TCTAC (SEQ ID NO: 26) | AGAAGTAAAAGTA ATAATTATGCA (SEQ ID NO: 27) | CATGGTAACTACTACTTTG ACTAC (SEQ ID NO: 28) |
| 1A6 | GGATTCACTTTCAGT AGCTTT (SEQ ID NO: 34) | AGTAGTGGCAGTAG TACC (SEQ ID NO: 35) | AACCAATCCCCTACGG GGTTTGCTTAC (SEQ ID NO: 36) |

TABLE 10

Variable Heavy Chain CDR Sequences - Kabat

| | CDR1 | CDR2 | CDR3 |
|---|---|---|---|
| 4G11 | ATCTACGCC ATGAAC (SEQ ID NO: 29) | CGCATAAGAAGTAAAAGTAATAATT ATGCAACATATTATGCCG ATTCAATGAAAGAC (SEQ ID NO: 30) | CATGGTAACTACTA CTTTGACTAC (SEQ ID NO: 28) |
| 1A6 | AGCTTTGGA ATGCAC (SEQ ID NO: 37) | TACATTAGTAGTGGCAGTAGT ACCATCTACTATGCAGACACA GTGAAGGGC (SEQ ID NO: 38) | AACCAATCCCCT ACGGGGTTTGCTTA C (SEQ ID NO: 36) |

The isolated nucleic acid molecule(s) (polynucleotides), encode a biologically relevant portion of 4G11 and/or 1A6, or affinity matured version or otherwise mutated version of 4G11 and/or 1A6 or other anti-tau antibodies discussed herein. To this end, the isolated nuclei acid molecules(s) may include one or more of the foregoing DNA sequences, a fragment of one or more of the foregoing sequences, or a nucleic acid sequence that at least 70% homologous, 80% homologous, 90% homologous or 99% homologous to one or more of the foregoing.

Nucleic acids of the present invention may be substantially free from other nucleic acids. For most cloning purposes, DNA is a preferred, but non-limiting, nucleic acid. One or a combination of the foregoing DNA molecules may be subcloned into an expression vector and subsequently transfected into a host cell of choice wherein the recombinant host cell provides a source for substantial levels of a relevant portion of the 4G11 and/or 1A6, or anti-tau antibody of the present invention, or the affinity matured version thereof. Such procedures may be used for a variety of utilities, such as generating scFvs or for co-expressing these $V_H$ and $V_L$ chains in a mammalian expression vector system which encodes human $C_H$ and $C_L$ regions, of for example, an IgG antibody.

The degeneracy of the genetic code is such that, for all but two amino acids, more than a single codon encodes a particular amino acid. This allows for the construction of synthetic DNA that encodes an antibody of the present invention where the nucleotide sequence of the synthetic DNA differs significantly from the nucleotide sequences disclosed herein, but still encodes such an antibody, or fragments thereof. Such synthetic DNAs are intended to be within the scope of the present invention. If it is desired to express such synthetic DNAs in a particular host cell or organism, the codon usage of such synthetic DNAs can be adjusted to reflect the codon usage of that particular host, thus leading to higher levels of expression of the an antibody of the present invention. In other words, this redundancy in the various codons which code for specific amino acids is within the scope of the present invention. Therefore, this invention is also directed to those DNA sequences which encode RNA comprising alternative codons which code for the eventual translation of the identical amino acid, as shown below: A=Ala=Alanine: codons GCA, GCC, GCG, GCU; C=Cys=Cysteine: codons UGC, UGU; D=Asp=Aspartic acid: codons GAC, GAU E=Glu=Glutamic acid: codons GAA, GAG; F=Phe=Phenylalanine: codons UUC, UUU; G=Gly=Glycine: codons GGA, GGC, GGG, GGU; H=His=Histidine: codons CAC, CAU; I=Ile=Isoleucine: codons AUA, AUC; AUU; K=Lys-Lysine: codons AAA, AAG; L=Leu=Leucine: codons UUA, UUG, CUA, CUC, CUG, CUU; M=Met=Methionine: codon AUG; N=Asp=Asparagine: codons GAU, GAC; P=Pro=Proline: codons CCA, CCC, CCG, CCU; Q=Gln=Glutamine: codons CAA, CAG; R=Arg=Arginine: codons AGA, AGG, CGA, CGC, CGG, CGU; S=Ser=Serine: codons AGC, AGU, UCA, UCC, UCG, UCU; T=Thr=Threonine: codons ACA, ACC, ACG, ACU; V=Val=Valine: codons GUA, GUC, GUG, GUU; W=Trp=Tryptophan: codon UGG; Y=Tyr=Tyrosine: codons UAC, UAU. Such recombinant expression vectors may then be stably or transiently transfected into an appropriate cell line for the generation of alternative antibody form.

The present invention notes the existence of codon redundancy which may result in differing DNA molecules expressing an identical antibody or portion thereof (e.g., alternative nucleic acid molecules encoding an identical scFv or a $V_H$ and/or $V_L$ portion of an IgG). For purposes of this specification, a sequence bearing one or more replaced codons will be defined as a degenerate variation. Another source of sequence variation may occur through RNA editing. Such RNA editing may result in another form of codon redundancy, wherein a change in the open reading frame does not result in an altered amino acid residue in the expressed protein. Also included within the scope of this invention are mutations either in the DNA sequence or the translated antibody which improve the ultimate physical properties of the expressed antibody. To this end, the present invention relates to (i) affinity matured versions of anti-tau antibodies, including but not limited to 4G11 and/or 1A6, and/or (ii) mutated forms of an anti-tau antibody, including but not limited to 4G11 and/or 1A6, including but not limited to one or more mutations in the CDR1, CDR2 and/or CDR3 regions as generated through known affinity maturation methodology and recombinant DNA techniques known for introducing site specific mutation. Such isolated or purified nucleic acid molecules will represent the $V_H$ and/or $V_L$ portions of the anti-tau antibody. These nucleic acids are substantially free from other nucleic acids and may be cloned in accordance with the foregoing.

The present invention also relates to recombinant vectors and recombinant hosts, both prokaryotic and eukaryotic, which contain nucleic acid molecules encoding the respective heavy and/or light regions (or fragments thereof) of an anti-tau antibody. These nucleic acid molecules, in whole or in part, can be linked with other DNA molecules (i.e, DNA molecules which encompass immunoglobulin genes used for generation of a recombinant human antibody) that are not naturally linked, to form "recombinant DNA molecules" which encode a respective human recombinant antibody. These vectors may be comprised of DNA or RNA. For most cloning purposes DNA vectors are preferred. Typical vectors include plasmids, modified viruses, bacteriophage, cosmids, yeast artificial chromosomes, and other forms of episomal or integrated DNA. It is within the purview of the skilled artisan to determine an appropriate vector for a particular gene transfer, generation of a recombinant human antibody or other use. Methods of subcloning nucleic acid molecules of interest into expression vectors, transforming or transfecting host cells containing the vectors, and methods of making substantially pure protein comprising the steps of introducing the respective expression vector into a host cell, and cultivating the host cell under appropriate conditions are well known. The antibody (such as an IgG recombinant human antibody) so produced may be harvested from the host cells in conventional ways. Any known expression vector may be utilized to practice this portion of the invention, including any vector containing a suitable promoter and other appropriate transcription regulatory elements. The resulting expression construct is transferred into a prokaryotic or eukaryotic host cell to produce recombinant protein. Expression vectors are defined herein as DNA sequences that are required for the transcription of cloned DNA and the translation of their mRNAs in an appropriate host. Such vectors can be used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Techniques for such manipulations can be found described in Sambrook, et al. (1989, Molecular Cloning. A Laboratory Manual; Cold Spring Harbor Laboratory, Cold Spring Harbor, N.Y.) are well known and available to the artisan of ordinary skill in the art. Expression vectors may include, but are not limited to, cloning vectors, modified cloning vectors, specifically designed plasmids or viruses. Commercially available mammalian expression vectors which may be suitable, include, but are not limited to, pcDNA3.neo (Invitrogen), pcDNA3.1 (Invitrogen), pCI-neo (Promega), pLITMUS28, pLITMUS29, pLITMUS38 and pLITMUS39 (New England Bioloabs), pcDNAI, pcDNAIanp (Invitrogen), pcDNA3 (Invitrogen), pMClneo (Stratagene), pXT1 (Stratagene), pSG5 (Stratagene), EBO pSV2-neo (ATCC 37593) pBPV-1(8-2) (ATCC 37110), pdBPV-MMTneo (342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565). Also, a variety of bacterial expression vectors are available, including but not limited to pCR2.1 (Invitrogen), pET1 1a (Novagen), lambda gt1 1 (Invitrogen), and pKK223-3 (Pharmacia). In addition, a variety of fungal cell expression vectors may be used, including but not limited to pYES2 (Invitrogen) and Pichie expression vector (Invitrogen). Also, a variety of insect cell expression vectors may be used, including but are not limited to pBlueBacIII and pBlueBacHis2 (Invitrogen), and pAcG2T (Pharmingen).

Recombinant host cells may be prokaryotic or eukaryotic, including but not limited to, bacteria such as *E. coli*, fungal cells such as yeast, mammalian cells including, but not limited to, cell lines of bovine, porcine, monkey and rodent origin; and insect cells. Mammalian species which may be suitable,—26 include but are not limited to, L cells L-M (TK-) (ATCC CCL1.3), L cells L-M (ATCC CCL 1.2), Saos-2 (ATCC HTB-85), 293 (ATCC CRL1573), Raji (ATCC CCL 86), CV-1 (ATCC CCL 70), COS-1 (ATCC CRL1650), COS-7(ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1(ATCC CCL 26), MRC-5 (ATCC CCL171) and CPAE (ATCC CCL 209).

The antibodies of the present invention may also be adapted or specifically engineered to form variants of the foregoing, including, but not limited to, a polyclonal, alternative monoclonal, chimeric, and/or humanized antibodies. Isolated or variant antibodies of the invention may include single variable domains (sVDs) and antigen binding proteins that comprise sVDs. sVD binding sites can be obtained from antigen specific Fv regions (which comprise both $V_H$ and $V_L$ domains). Often, it can be shown that the binding affinity and specificity of an Fv region is contributed primarily by one of the variable domains. Alternatively, the scFv can be obtained directly. Direct sources of sVDs include mammals (e.g., camelids) that naturally express antibodies containing only $V_H$ domain. Further, phage display libraries can be constructed to express only a single variable domain. For example, a human domain antibody phage display library is commercially available from Domantis (Cambridge, UK).

Chimeric antibodies may generally comprise variable domains of one antibody and constant domains of a different antibody. Typically, to minimize host immune responses against the antibody and to enhance host responses against the antibody target by retaining antibody effector functions, the constant domains of a chimeric antibody are taken from the same species to which the chimeric antibody will be administered.

Humanized antibodies are a form of a chimeric protein that are constructed such that the variable domains include one or more complementarity determining regions (CDRs) of non-human origin that are grafted to human framework regions. The non-human amino acid residues are often referred to as "import" residues, and are typically taken from an "import" variable domain. Humanization can be performed generally following the method of Winter and co-workers (Jones et al., 1986, Nature 321:522-525; Riechmann et al., 1988, Nature, 332:323-327; Verhoeyen et al., 1988, Science 239:1534-1536), by substituting rodent CDRs or CDR sequences for the corresponding sequences of a human antibody. Accordingly, such "humanized" antibodies are chimeric antibodies (see, e.g., U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in non-human, for example, rodent antibodies. The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework. (FR) for the humanized antibody (Sims et al., 1987, J. Immunol. 151:2296; Chothia et al., 1987, J. Mol. Biol. 196:901). Another method uses a particular framework derived from the consensus sequence of all human antibodies of a particular subgroup of light or heavy chains. The same framework may be used for several different humanized antibodies (Carter et al., 1992, Proc. Natl. Acad. Sci. USA 89:4285; Presta et al., 1993, J. Immunol. 151:2623). To this end, and in certain embodiments, is may be generated by various means of recombinant DNA technology and non-human transgenics that are well known in the art. Such methodology is utilized to generate an antibody from one or the following origins: (i) a scFv or alternative antibody isolated from a combinatorial human antibody library; (ii) a partial or complete antibody generated from a respective expression vector stably or transiently transfected into a host cell, preferably a mammalian host cell (e.g., subcloning nucleotide sequences encoding $V_H$ and $V_L$ chains into an expression vector in conjunction with respective $C_H$ and $C_L$ nucleotide sequences, so as to promote expression of a predetermined form of antibody showing specificity to tau; and/or (iii) an antibody isolated from a non-human transgenic animal which contains human immunoglobulin genes, or by any other known methodology which relies on the recombinant 'mixing and matching' of human immunoglobulin gene sequences to other DNA sequences in order to generate the human recombinant antibody of interest.

A humanized construct is valuable for elimination of adverse immunogenic characteristics, for example, where an antigen binding domain from a non-human source is desired to be used for treatment in a human. Variable domains have a high degree of structural homology, allowing easy identification of amino acid residues within variable domains which correspond to CDRs and FRs.

Methods have been developed to preserve or to enhance affinity for such variant antibodies, particularly, though not exclusively, the chimeric and/or humanized forms. One way is to include in the recipient variable domain the foreign framework residues which influence the conformation of the CDR regions. A second way is to graft the foreign CDRs onto human variable domains with the closest homology to the foreign variable region. CDRs are most easily grafted onto different framework regions by first amplifying individual FR sequences using overlapping primers which include desired CDR sequences, and joining the resulting gene segments in subsequent amplification reactions. Grafting of a CDR onto a different variable domain can further involve the substitution of amino acid residues which are adjacent to the CDR in the amino acid sequence or packed against the CDR in the folded variable domain structure which affect the conformation of the CDR. Humanized variable domains of the invention therefore include human domains which comprise one or more non-human CDRs as well as such domains in which additional substitutions or replacements have been made to preserve or enhance binding characteristics.

It is of additional import that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e, the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding. Humanization of antibodies is a straightforward protein engineering task. Nearly all murine antibodies can be humanized by CDR grafting, resulting in the retention of antigen binding. See, Lo, Benny, K. C., editor, in Antibody Engineering: Methods and Protocols, volume 248, Humana Press, New Jersey, 2004. To this end, to merely reiterate, additional embodiments of the invention relate to human, humanized, chimeric, affinity matured, mutated, or other forms of anti-Aβ antibodies generated from a 4G11-based mAb or a 1A6-based mAb.

Antibodies of the present invention may also employ variable domains that have been made less immunogenic by replacing surface-exposed residues so as to make the antibody appear as self to the immune system. Antibodies have been modified by this process with no loss of affinity. Because the internal packing of amino acid residues in the vicinity of the antigen binding site remains unchanged, affinity is preserved. Substitution of surface-exposed residues according to the invention for the purpose of reduced immunogenicity does not mean substitution of CDR residues or adjacent residues which influence binding characteristics.

In any of the foregoing embodiments, the variable regions, CDRs, and constant regions incorporated into antibodies can be subject to in vitro or in vivo mutation and screening procedures in order to modify affinity and/or specificity. Thus, binding domains of the invention include those for which binding characteristics have been improved by mutating CDRs and/or FR regions by direct mutation, methods of affinity maturation, or chain shuffling. It is understood that amino acid residues that are primary determinants of binding of single domain antibodies can be within Kabat or Chothia defined CDRs, but may include other residues as well. For sVDs, residues important for antigen binding can also potentially include amino acids that would otherwise be located at the interface of a $V_H$-$V_L$ heterodimer. Typically, phage display is used to screen such mutants to identify those having the desired binding characteristics (see, e.g., Yang et al., J. Mol. Biol., 254: 392-403 (1995)). Mutations can be made in a variety of ways. One way is to randomize individual residues or combinations of residues so that in a population of otherwise identical sequences, all twenty amino acids or a subset thereof are found at particular positions. Alternatively, mutations may be induced over a range of CDR residues by error prone PCR methods (see, e.g., Hawkins et al., J. Mol. Biol., 226: 889-896 (1992)). For example, phage display vectors containing heavy and light chain variable region genes may be propagated in mutator strains of E. coli (see, e.g., Low et al., J. Mol. Biol., 250: 359-368 (1996)). These methods of mutagenesis are illustrative of the many methods known to one of skill in the art.

Although the invention has been described with reference to certain embodiments, it will be understood by those skilled in the art that various changes may be made and equivalents may be substituted for elements thereof without departing from the scope of the invention. In addition, many modifications may be made to adapt to a particular situation or material to the teachings of the invention without departing from the essential scope thereof. Therefore, it is intended that the invention not be limited to the particular embodiments disclosed, but that the invention will include all embodiments falling within the scope of the appended claims or any claims later added.

The anti-tau antibodies of the present invention may be used alone or within compositions for a wide array uses. In certain aspects, antibodies and compositions containing antibodies of the present invention may be used for diagnosing and/or treating a patient diagnosed with a disease state characterized, at least in part, by tau activity, and in certain aspects by the self-assembly of tau protein. In further aspects, such antibodies may be used for detection of tau expression in a cell, screening for and selecting alternative tau binding compounds, or the like. The following elaborates on such uses, but is not to be considered limiting to the uses of the anti-tau antibodies of the present invention. To this end, one of skill in the art will readily appreciate that the antibodies of the present invention may be provided with any use otherwise known in the art.

Treatment Methods and Pharmaceutical Formulations

In certain aspects, the anti-tau antibodies of the present invention may be administered to a subject for treating, preventing, delaying, or otherwise monitoring onset of one or more symptoms associated with a neurodegenerative tauopathy in a subject. Such symptoms can be, but are not limited to, the formation of pathological tau deposits, hyperphosphorylated tau deposits, insoluble tau deposits, neurofibrillary fibers, pre-tangle phosphor tau aggregates, intraneuronal neurofibrillary tangles or extraneuronal neurofibrillary tangles in the brain or spinal cord of a subject. The symptom also, or alternatively, may be an increase in tau protein concentration in the subject's serum, blood, urine, or cerebrospinal fluid, as compared to a healthy subject not having the neurodegenerative tauopathy. The symptom can also, or alternatively be a neurological symptom, such as, but not limited to, altered taste aversions, altered contextual fear conditioning, memory impairment, loss of motor function, and the like.

A neurodegenerative tauopathy refers to any disease state associated (or otherwise characterized as including) the pathological aggregation of tau protein, particularly though not exclusively, in the brain or spinal cord. As noted above, such aggregation may include the formation of pathological tau deposits, hyperphosphorylated tau deposits, insoluble tau deposits, neurofibrillary fibers, pre-tangle phosphor tau aggregates, intraneuronal neurofibrillary tangles or extraneuronal neurofibrillary tangles in the brain or spinal cord of a subject. Non-limiting examples of such diseases include Alzheimer's disease, amyotrophic lateral sclerosis/parkinsonism-dementia complex, argyrophilic grain dementia, British type amyloid angiopathy, cerebral amyloid angiopathy, corticobasal degeneration, Creutzfeldt-Jakob disease, dementia pugilistica, diffuse neurofibrillary tangles with calcification, Down's syndrome, frontotemporal dementia, frontotemporal dementia with parkinsonism linked to chromosome 17, frontotemporal lobar degeneration, Gerstmann-Straussler-Scheinker disease, Hallervorden-Spatz disease, inclusion body myositis, multiple system atrophy, myotonic dystrophy, Niemann-Pick disease type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, subacute sclerosing panencephalitis, tangle only dementia, multi-infarct dementia and ischemic stroke. In certain non-limiting aspects, the disease state is Alzheimer's disease.

The term "treatment," as noted above, refers to both therapeutic and prophylactic measures. Those in need of treatment include those already afflicted with the disease or disorder as well as those in which the disease or disorder is to be prevented. The subject to be treated may have been diagnosed as having the disease or disorder or may be predisposed or susceptible to the disease.

Administration of the anti-tau antibodies may be alone or in combination with existing therapeutic regimens for the neurodegenerative tauopathy. With Alzheimer's disease, for example, the additional therapeutic regimens can include one or a plurality of agents, small molecules, or biologics otherwise known in the art. Those skilled in the art are readily able to determine standard dosages and scheduling for each of these regimens.

In certain aspects, the dosage regimen will be determined by an attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg (or of nucleic acid for expression or for inhibition of expression in this range); however, doses below or above this exemplary range are envisioned, especially considering the aforementioned factors. Generally, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, or at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimens entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated. Progress can be monitored by periodic assessment. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like. Furthermore, the pharmaceutical composition of the invention can comprise further agents such as dopamine or psychopharmacologic drugs, depending on the intended use of the pharmaceutical composition.

In conjunction with one or more of the foregoing treatment regimes, a pharmaceutical composition comprising an effective amount one more of the anti-tau antibodies of the present invention, or an affinity matured version thereof, may be administered to provide a prophylactic or therapeutic treatment by inhibiting tau activity or, in particular, tau aggregation. The antibody-based pharmaceutical composition of the present invention may be formulated by any number of strategies known in the art (e.g., see McGoff and Scher, 2000, *Solution Formulation of Proteins/Peptides*: In McNally, E. J., ed. *Protein Formulation and Delivery*. New York, N.Y.: Marcel Dekker; pp. 139-158; Akers and Defilippis, 2000, *Peptides and Proteins as Parenteral Solutions*. In: *Pharmaceutical Formulation Development of Peptides and Proteins*. Philadelphia, Pa.: Talyor and Francis; pp. 145-177; Akers, et al., 2002, *Pharm. Biotechnol.* 14:47-127). A pharmaceutically acceptable composition suitable for patient administration will contain an effective amount of the antibody in a formulation which both retains biological activity while also promoting maximal stability during storage within an acceptable temperature range. The pharmaceutical compositions can also include, depending on the formulation desired, pharmaceutically acceptable diluents, pharmaceutically acceptable carriers and/or pharmaceutically acceptable excipients, or any such vehicle commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution or the like. The amount of an excipient that is useful in the pharmaceutical composition or formulation of this invention is an amount that serves to uniformly distribute the antibody throughout the composition so that it can be uniformly dispersed when it is to be delivered to a subject in need thereof. It may serve to dilute the antibody to a concentration which provides the desired beneficial palliative or curative results while at the same time minimizing any adverse side effects that might occur from too high a concentration. It may also have a preservative effect. Thus, for the antibody having a high physiological activity, more of the excipient will be employed. On the other hand, for any active ingredient(s) that exhibit a lower physiological activity, a lesser quantity of the excipient will be employed. In general, the amount of excipient in the composition will be between about 50% weight (w) and 99.9% wt of the total composition. If the antibody exhibits a particularly low physiological activity, the amount of excipient could be as little as 1% wt. On the other hand, for an antibody that has a particularly high physiological activity, the amount of excipient may be between about 98.0% and about 99.9% wt. In addition, the antibody or antibodies may be administered in the form of a "chemical derivative" (a molecule that contains additional chemical moieties which are not normally a part of the base molecule). Such moieties may improve the solubility, half-life, absorption, etc. of the biological agent. Alternatively, these moieties may attenuate undesirable side effects of the antibody.

Pharmaceutical compositions can also include large, slowly metabolized macromolecules such as proteins, polysaccharides, polylactic acids, polyglycolic acids and copolymers (such as latex functionalized sepharose, agarose, cellulose, and the like), polymeric amino acids, amino acid copolymers, and lipid aggregates (such as oil droplets or liposomes). Additionally, these carriers can function as immunostimulating agents (i.e., adjuvants). For parenteral administration, agents of the invention can be administered as injectable dosages of a solution or suspension of the substance in a physiologically acceptable diluent with a pharmaceutical or physiologically acceptable carrier which can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

The antibody formulation may be in liquid form or solid form. A solid formulation is generally lyophilized and brought into solution prior to administration for either single or multiple dosing. The formulations should not be exposed to extreme temperature or pH so as to avoid thermal denaturation. Thus, it is essential to formulate an antibody composition of the present invention within a biologically relevant pH range. A solution buffered to maintain a proper pH range during storage is indicated, especially for liquid formulations stored for longer periods of time between formulation and administration. To date, both liquid and solid formulations require storage at lower temperatures (usually 2-8° C.) in order to retain stability for longer periods. Formulated antibody compositions, especially liquid formulations, may contain a bacteriostat to prevent or minimize proteolysis during storage, including but not limited to effective concentrations (usually <1% w/v) of benzyl alcohol, phenol, m-cresol, chlorobutanol, methylparaben, and/or propylparaben. A bacteriostat may be contraindicated for some patients. Therefore, a lyophilized formulation may be reconstituted in a solution either containing or not containing such a component. Additional components may be added to either a buffered liquid or solid antibody formulation, including but not limited to sugars as a cryoprotectant (including but not necessarily limited to polyhydroxy hydrocarbons such as sorbitol, mannitol, glycerol and dulcitol and/or disaccharides such as sucrose, lactose, maltose or trehalose) and, in some instances, a relevant salt (including but not limited to NaCl, KCl or LiCl). Such antibody formulations, especially liquid formulations slated for long term storage, will rely on a useful range of total osmolarity to both promote long term stability at temperature of 2-8° C., or higher, while also making the formulation useful for parenteral injection. An effective range of total osmolarity (the total number of molecules in solution) is from about 200 mOs/L to about 800 mOs/L. It will be apparent that the amount of a cyroprotectant, such as sucrose or sorbitol, will depend upon the amount of salt in the formulation in order for the total osmolarity of the solution to remain within an appropriate range. Therefore a salt free formulation may contain from about 5% to about 25% sucrose, with a preferred range of sucrose from about 7% to about 15%, with an especially preferred sucrose concentration in a salt free formulation being from 10% to 12%. Alternatively, a salt free sorbitol-based formulation may contain sorbitol within a range from about 3% to about 12%, with a preferred range from about 4% to 7%, and an especially preferred range is from about 5% to about 6% sorbitol in a salt-free formulation. Salt-free formulations will of course warrant increased ranges of the respective cryoprotectant in order to maintain effective osmolarity levels. These formulation may also contain a divalent cation (including but not necessarily limited to $MgCl_2$, $CaCl_2$ and $MnCl_2$); and a non-32 ionic surfactant (including but not necessarily limited to Polysorbate-80 (Tween 80®), Polysorbate-60 (Tween 60®), Polysorbate-40 (Tween 40®) and Polysorbate-20 (Tween 20®), polyoxyethylene alkyl ethers, including but not limited to Brij 58®, Brij 35®, as well as others such as Triton X-100®, Triton X 114®, NP40®, Span 85 and the Pluronic series of non-ionic surfactants (e.g., Pluronic 121)). Any combination of such components, including probable inclusion of a bacteriostat, may be useful to fill the antibody-containing formulations of the present invention.

Numerous examples of various other carriers, diluents, excipients and the such are known in the art and are disclosed in references cited herein, as well as *Remington's Pharmaceutical Sciences* (18th ed.; Mack Publishing Company, Easton, Pa., 1990), the contents of which are incorporated herein by reference. Briefly, it will be appreciated that suitable carriers, excipients, and other agents may be incorporated to formulate the pharmaceutical compositions to provide improved transfer, delivery, tolerance, and the like. The methods of incorporating the biological agent and/or additional active ingredient(s) into the carrier are known to a person of ordinary skill in the art and depend on the nature of the biological agent and the nature of the carrier selected by a person practicing the current invention. Ionic binding, gel encapsulation or physical trapping inside the carrier, iontophoresis and soaking the carrier in a solution of the biological agent are suitable examples contemplated in formulating a pharmaceutical composition to be used to practice of the disclosed treatment methods. Alternatively, the carrier may be little more than a diluent for the biological agent. These formulations may include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax. The dosage regimen utilizing the compounds of the present invention is selected in accordance with a variety of factors including type, species, age, weight, sex and medical condition of the patient; the severity of the condition to be treated; the route of administration; the renal, hepatic and cardiovascular function of the patient; and the particular biological agent thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug. Any of the foregoing formulations may be appropriate in treatments and therapies in accordance with the present invention, provided that the active ingredient in the formulation is not inactivated by the formulation and the formulation is physiologically compatible.

The pharmaceutical compositions of the present invention may be administered to the host in any manner, strategy and/or combination available in the art in amounts sufficient to offer a therapeutic treatment by inhibiting, delaying, treating or reducing, tau protein aggregation. These compositions may be provided to the individual by a variety of routes known in the art, especially parenteral routes, including but in no way limited to parenteral routes such as intravenous (IV), intramuscular (IM); or subcutaneous (SC) administration, with IV administration being the norm within the art of therapeutic antibody administration. These compositions may be administered as separate or multiple doses (i.e, administration of the antibody at staggered times by maintaining the sterile condition of the formulation through the treatment regime). The dosage regimen utilizing the compounds of the present invention is selected in accordance with a variety of factors including type, species, age, weight, sex and medical condition of the patient (such as a human patient); the severity of the condition to be treated; the route of administration; the renal, hepatic and cardiovascular function of the patient; and the particular antibody thereof employed. A physician or veterinarian of ordinary skill can readily determine and prescribe the effective therapeutic amount of the antibody. Optimal precision in achieving concentrations of antibody within the range that yields efficacy without toxicity requires a regimen based on the kinetics of the drug's availability to target sites. This involves a consideration of the distribution, equilibrium, and elimination of a drug. Antibodies described herein may be used alone at appropriate dosages. Alternatively, co-administration or sequential administration of other agents may be desirable. It will be possible to present a therapeutic dosing regimen for the antibodies of the present invention in conjunction with administration of alternative prophylactic or therapeutic regimes. An effective dosage regime will vary depending upon many different factors, including means of administration, target site, physiological state of the patient, whether the patient is human or an animal, other medications administered, and whether treatment is prophylactic or therapeutic. For administration of an anti-tau antibody, the dosage ranges from about 0.0001 to 100 mg/kg, and more usually 0.01 to 5 mg/kg of the host body weight.

Another aspect regarding delivery and dosage regimes for an anti-tau antibody composition of the present invention relates to drug delivery via parenteral routes, which may include non-injectable and injectable devices. Typically, injectable compositions are prepared as either liquid solutions or suspensions; solid forms suitable for solution in, or suspension in, liquid vehicles prior to injection can also be prepared. The preparation also can be emulsified or encapsulated in liposomes or microparticles such as polylactide, polyglycolide, or copolymer for enhanced adjuvant effect, as discussed above (see Langer, 1990, Science 249: 1527-1523; and Hanes, 1997, Advanced Drug Delivery Reviews 28: 97-119). The agents of this invention can be administered in the form of a depot injection or implant preparation which can be formulated in such a manner as to permit a sustained or pulsatile release of the active ingredient.

Vaccine

In certain embodiments, the foregoing pharmaceutical composition(s) can be formulated as a vaccine, for example, if the pharmaceutical composition of the invention includes an anti-tau antibody or binding fragment, derivative or variant thereof for passive immunization. Phosphor-tau species have been previously reported to be present extracellularly in plasma and CSF (Aluise et al, Biochim. Biophys. Acta. 1782 (2008), 549-558) and studies in transgenic mouse lines using active vaccination with phosphorylated tau peptides revealed reduced brain levels of tau aggregates in the brain and slowed progression of behavior impairments (Sigurdsson, J. Alzheimers Dis. 15 (2008), 157-168; Boimel et al, Exp Neurol. 224 (2010), 472-485). Accordingly, it is prudent to expect that passive immunization with one or more of the anti-tau antibodies discussed herein and equivalent tau binding molecules of the present invention would help to circumvent several adverse effects of active immunization therapy concepts as discussed above. Therefore, the present anti-tau antibodies and their equivalents of the present invention will be particularly useful as a vaccine for the prevention or amelioration of neurodegenerative tauopathy, particularly those discussed herein, and in certain preferred embodiments Alzheimer's disease.

Tau Detection/Diagnosis Assays

The anti-tau antibodies described herein may be used as the basic reagents in a number of different immunoassays to determine the presence of a tau isoform in a tissue sample and/or diagnose the presence of aggregated tau protein, including, but not limited to tau deposits, hyperphosphorylated tau deposits, insoluble tau deposits, neurofibrillary fibers, pre-tangle phosphor tau aggregates, intraneuronal neurofibrillary tangles or extraneuronal neurofibrillary tangles. Generally speaking, the antibodies can be employed in any type of immunoassay, whether qualitative or quantitative. This includes both the two-site sandwich assay and the single site immunoassay of the non-competitive type, as well as in traditional competitive binding assays. One embodiment of interest, for ease of detection, and its quantitative nature, is the sandwich or double antibody assay, of which a number of variations exist, all of which are intended to be encompassed by this portion of the present invention. For example, in a typical forward sandwich assay, unlabeled antibody (e.g. a first anti-tau antibody) is immobilized on a solid substrate, e.g., microtiter plate wells, and the sample to be tested is brought into contact with the bound molecule. After a suitable period of incubation, for a period of time sufficient to allow formation of an antibody-antigen binary complex, a second antibody (e.g. a second anti-tau antibody with a different target epitope than the first), labeled with a reporter molecule capable of inducing a detectable signal, is then added and incubation is continued allowing sufficient time for binding with the antigen at a different site and the formation of a ternary complex of antibody-antigen-labeled antibody. Any unreacted material is washed away, and the presence of the antigen is determined by observation of a signal, which may be quantitated by comparison with a control sample containing known amounts of antigen. Variations on the forward sandwich assay include the simultaneous assay, in which both sample and antibody are added simultaneously to the bound antibody, or a reverse sandwich assay in which the labeled antibody and sample to be tested are first combined, incubated and added to the unlabelled surface bound antibody. These techniques are well known to those skilled in the art, and the possibility of minor variations will be readily apparent. As used herein, "sandwich assay" is intended to encompass all variations on the basic two-site technique.

For the sandwich assays of the present invention, the only limiting factor is that both antibodies have different binding specificities for the tau protein. Thus, a number of possible combinations are possible. As a more specific example, in a typical forward sandwich assay, a primary antibody is either covalently or passively bound to a solid support. The solid surface is usually glass or a polymer, the most commonly used polymers being cellulose, polyacrylamide, nylon, polystyrene, polyvinylchloride or polypropylene. The solid supports may be in the form of tubes, beads, discs or microplates, or any other surfaces suitable for conducting an immunoassay. The binding processes are well known in the art. Following binding, the solid phase-antibody complex is washed in preparation for the test sample. An aliquot of the body fluid to be tested is then added to the solid phase complex and incubated at 25° C. for a period of time sufficient to allow binding of any tau protein present to the antibody. The second antibody is then added to the solid phase complex and incubated at 25° C. for an additional period of time sufficient to allow the second antibody to bind to the primary antibody-antigen solid phase complex. The second antibody is linked to a reporter molecule, the visible signal of which is used to indicate the binding of the second antibody to any antigen in the sample. By "reporter molecule," as used in the present specification is meant a molecule which by its chemical nature, provides an analytically detectable signal which allows the detection of antigen-bound antibody. Detection must be at least relatively quantifiable, to allow determination of the amount of antigen in the sample, this may be calculated in absolute terms, or may be done in comparison with a standard (or series of standards) containing a known normal level of antigen.

The most commonly used reporter molecules in this type of assay are either enzymes or fluorophores. In the case of an enzyme immunoassay an enzyme is conjugated to the second antibody, often by means of glutaraldehyde or periodate. As will be readily recognized, however, a wide variety of different conjugation techniques exist, which are well known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product rather than the chromogenic substrates noted above. In all cases, the enzyme-labeled antibody is added to the first antibody-tau protein complex and allowed to bind to the complex, and then the excess reagent is washed away. A solution containing the appropriate substrate is then added to the tertiary complex of antibody-antigen-labeled antibody. The substrate reacts with the enzyme linked to the second antibody, giving a qualitative visual signal, which may be further quantitated, usually spectrophotometrically, to give an evaluation of the amount of antigen that is present in the serum sample.

Additionally, fluorescent compounds, such as fluorescein or rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope. As in the enzyme immunoassay (EIA), the fluorescent-labeled antibody is allowed to bind to the first antibody-tau protein complex. After washing the unbound reagent, the remaining ternary complex is then exposed to light of the appropriate wavelength, and the fluorescence observed indicates the presence of the antigen. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

In another embodiment, the sample to be tested may be used in a single site immunoassay wherein it is adhered to a solid substrate either covalently or noncovalently. An unlabeled anti-tau antibody of the present invention is brought into contact with the sample bound on the solid substrate. After a suitable period of incubation, for a period of time sufficient to allow formation of an antibody-antigen binary complex a second antibody, labeled with a reporter molecule capable of inducing a detectable signal, is then added and incubation is continued allowing sufficient time for the formation of a ternary complex of antigen-antibody-labeled antibody. For the single site immunoassay, the second antibody may be a general antibody (i.e zenogeneic antibody to immunoglobulin, particularly anti-(IgM and IgG) linked to a reporter molecule) that is capable of binding an antibody that is specific for tau.

In accordance with the foregoing, the anti-tau antibodies of the present invention can be used in a method for the diagnosis of a disorder in an individual by obtaining a body fluid sample from the tested individual which can be a blood sample, a lymph sample or any other body fluid sample and contacting the body fluid sample with an antibody of the instant invention under conditions enabling the formation of antibody-antigen complexes. The level of such complexes is then determined by methods known in the art, a level significantly higher than that formed in a control sample indicating the disease in the tested individual. In the same manner, the specific antigen bound by the antibodies of the invention can also be used. Thus, the present invention relates to an in vitro immunoassay comprising the binding molecule, e.g., antibody or antigen-binding fragment thereof of the invention.

In this context, the present invention also relates to means specifically designed for this purpose. For example, an antibody-based array can be used, which is for example loaded with anti-tau antibodies of the present invention which specifically recognize tau. Design of microarray immunoassays is summarized in Kusnezow et al, 2006, Mol. Cell Proteomics 5: 1681-1696. Accordingly, the present invention also relates to mieroarrays loaded with tau binding molecules identified in accordance with the present invention.

In one embodiment, the present invention relates to a method of diagnosing a tauopathic disease in a subject, the method comprising determining the presence of tau and/or pathologically modified and/or aggregated tau in a sample from the subject to be diagnosed with at least one antibody of the present invention, an tau binding fragment thereof or an tau-binding molecule having substantially the same binding specificities of any one thereof, wherein the presence of pathologically modified and/or aggregated tau is indicative of a neurodegenerative tauopathy and an increase of the level of the pathologically modified and/or aggregated tau in comparison to the level of the physiological tau forms is indicative for progression of a neurodegenerative tauopathy in said subject.

The subject to be diagnosed can be asymptomatic or preclinical for the disease. In one embodiment, the control subject has a tauopathic disease, for example, AD, ALS-PDC, AGD, CBD, CJD, FTD, FTDP-17, NP-C, PiD, PSP or other tauopathies as mentioned before, wherein a similarity between the level of pathologically modified and/or aggregated tau and the reference standard indicates that the subject to be diagnosed has a tauopathic disease. Alternatively, or in addition as a second control the control subject does not have a tauopathic disease, wherein a difference between the level tau and/or of pathologically modified and/or aggregated tau and the reference standard indicates that the subject to be diagnosed has a tauopathic disease. In one embodiment, the subject to be diagnosed and the control subject(s) are age-matched. The sample to be analyzed can be any body fluid suspected to contain pathologically modified and/or aggregated tau, for example a blood, CSF, or urine sample.

The level tau and/or of pathologically modified and/or aggregated tau can be assessed by any suitable method known in the art comprising, e.g., analyzing tau by one or more techniques chosen from Western blot, immunoprecipitation, enzyme-linked immunosorbent assay (ELISA), radioimmunoassay (RIA), fluorescent activated cell sorting (FACS), two-dimensional gel electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/MS), and laser densitometry. In one embodiment, said in vivo imaging of tau comprises positron emission tomography (PET), single photon emission tomography (SPECT), near infrared (NIR) optical imaging or magnetic resonance imaging (MRJ).

In further embodiments, the anti-tau antibodies of the present invention may be used to study the aggregation of tau proteins and its role in the progression of one or more neurodegenerative tauopathies, including Alzheimer's disease. In certain non-limiting embodiments, the differential binding of such antibodies, (i.e 4G11 to four tau isoforms and 1A6 to six tau isoforms) can be used to study and differentiate which tau isoforms are involved in the formation of neurofibrillary tangles and what roles each isoforms plays in the formation of these structures. Methods associated with such use include those discussed herein, and otherwise known in the art.

In conjunction with such embodiments, the present invention also includes a kit for detecting tau protein that includes (1) an antibody or a fragment thereof, capable of specifically binding in vitro to an epitope of a tau protein; and, (2) a reagent that binds, directly, or indirectly, to said antibody or the fragment thereof. Such a kit provides a pharmaceutical or diagnosticising one or more containers filled with one or more of the above described ingredients, e.g. anti-tau antibody, binding fragment, derivative or variant thereof, polynucleotide, vector or cell of the present invention. Associated with such container(s) can be a notice in the form prescribed by a governmental agency regulating the manufacture, use or sale of pharmaceuticals or biological products, which notice reflects approval by the agency of manufacture, use or sale for human administration. In addition or alternatively the kit comprises reagents and/or instructions for use in appropriate diagnostic assays. The composition, e.g. kit of the present invention is of course particularly suitable for the risk assessment, diagnosis, prevention and treatment of a disorder which is accompanied with the presence of tau, and in particular applicable for the treatment of Alzheimer's disease (AD), amyotrophic lateral sclerosis/parkinsonism-dementia complex (ALS-PDC), argyrophilic grain dementia (AGD), British type amyloid angiopathy, cerebral amyloid angiopathy, corticobasal degeneration (CBD), Creutzieldt-Jakob disease (CJD), dementia pugilistica, diffuse neurofibrillary tangles with calcification, Down's syndrome, frontotemporal dementia, frontotemporal dementia with parkinsonism linked to chromosome 17 (FTDP-17), frontotemporal lobar degeneration, Gerstmann-Straussler-Scheinker disease, Hallervorden-Spatz disease, inclusion body myositis, multiple system atrophy, myotonic dystrophy, Niemann-Pick disease type C (NP-C), non-Guamanian motor neuron disease with neurofibrillary tangles, Pick's disease (PiD), postencephalitic parkinsonism, prion protein cerebral amyloid angiopathy, progressive subcortical gliosis, progressive supranuclear palsy (PSP), subacute sclerosing panencephalitis, tangle only dementia, multi-infarct dementia and ischemic stroke.

Drug Screening Assay

In further embodiments, the anti-tau antibodies of the present invention may be used in methods of screening for and selecting compounds which may act as an inhibitor of tau activity in a cell or otherwise may be used to prevent, reduce, treat, or otherwise monitor the presence of tau protein aggregation. Such methodology comprises utilizing an antibody with anti-tau affinity in various antibody/peptide/test compound interaction assays in order to select a compound which modulates tau activity/aggregation. The compound may be a non-proteinaceous organic or inorganic molecule, a peptide (e.g., as a potential prophylactic or therapeutic peptide vaccine), a protein, DNA (single or double stranded) or RNA (such as siRNA or shRNA). It will become evident upon review of the disclosure and teachings of this specification that any such peptide or small molecule which effectively competes with an anti-tau antibody of the present invention for binding to the epitope of the tau, represents a possible lead compound relating to prophylactic or therapeutic treatment of a disease state characterized by tau expression, overexpression, or aggregation, particularly a neurodegenerative tauopathy. To this end, interaction assays may be utilized for the purpose of high throughput screening to identify compounds that occupy or interact with the tau epitopes and displace the antibody.

Various antibody/antigen-based assays known in the art may be used in accordance with the foregoing, including, but not limited to, an ELISA assay, a radioimmune assay, a Western blot analysis, any homogenous assay relying on a detectable biological interaction not requiring separation or wash steps (e.g., see AlphaScreen from PerkinElmer) and/or SPR-based technology (e.g., see BIACore)). Compounds and/or peptide vaccine candidates identified through use of an anti-tau antibody may be detected by a variety of assays. The assay may be a simple "yes/no" assay to determine whether there is a change in the ability to form the known antibody/antigen complex, or may be made quantitative in nature by utilizing an assay such as an ELISA based assay, a homogenous assay, or an SPR-based assay. To this end, the present invention relates to any such assay, regardless of the known methodology employed, which measures the ability of a test compound to compete with an anti-tau antibody of the present invention.

The following are examples supporting the foregoing invention. They are not to be construed as limiting to the invention.

EXAMPLES

Example 1—Generation of Tau Protein Antibodies

Tau proteins were used to immunize mice for the production of monoclonal antibodies (mAbs) against these targets. A total of 6 antibodies (4 IgM, 1 IgA, and 1 IgG) were generated that bound to all tau proteins tested. A characterization of each of these antibodies is provided in Table 11, below.

More specifically, female Balb/c mice were immunized with one of the tau isoforms. In addition, three female Balb/c mice were immunized with all six Tau isoforms. For the initial subcutaneous injections, the immunogen was suspended in 200 µL of Complete Freund's adjuvant at a concentration of 12.5 µg/mL. All subsequent booster injections were intraperitoneally administered with the immunogen suspended in 500 µL of Complete Freund's adjuvant at a concentration of 12.5 µg/mL. The immunization progress of each mouse was monitored by ELISA analysis of the serum titer in which 100 ug of all six Tau isoforms were attached to separate wells as the solid phase.

Sera from mice immunized with purified versions of the 6 proteins individually were tested for binding to all 6 peptides individually using an ELISA. That is, 100 g vials of lyophilized Tau 352, Tau 381, Tau 383, Tau 410, Tau 412, and Tau 441 were hydrated separately with 100 µL Milli-Q Water, which yielded a 1.0 mg/mL solution with buffer content of 50 mM MES/100 mM NaCl/0.5 mM EGTA/pH 6.8. 20 µL of each of the six vials was then diluted into separate 10 mL aliquots of TBS pH 7.4. 100 ng of each of the six Tau isoforms was added to the wells of a 96-well Nunc MaxiSorp plate and incubated at 2-8° C. for 15 hours.

After 15 hours the wells of the plate were washed 3 times with 250 µL TBST (TBS with 0.1% Tween 20) pH 7.4. Following the washing steps, the wells were blocked with 250 µL TBS with 3% BSA (Fisher #BP1605-100) and incubated at 37° C. for 1 hour. After one hour, the wells were emptied and rinsed again 3 times with 250 µL TBST. The antibodies were prepared by dilution in TBST with 1% BSA to yield ratios of 1:500 (1A6) and 1:5000 (4G11). 50 µL of primary antibody solution was added to the wells, and the plate was incubated at 37° C. for 1 hour.

After one hour the plate was emptied and washed 5× with 250 µL TBST. The secondary antibody (Goat anti-mouse IgG (H+L) HRP Conjugate) was prepared at a 1:5,000 dilution in TBST with 1% BSA. 50 µL of this secondary antibody solution was then added to every well on the plate and incubated at 25° C. for 1 hour.

After one hour the wells of the plate were emptied and washed 5 times with TBST. After the final wash 100 µL of 1-Step Ultra TMB-ELISA (Thermo Scientific #34028) was added to each well and allowed to incubate for 15 minutes in the dark at 25° C. 100 µL of 2M Sulfuric Acid was added to each well, and the plate was analyzed at 450 nm using a SpectraMAX190 by Molecular Devices.

FIG. 1 illustrates the ELISA results from the serum sample. Titers at zero represent mice that were harvested for fusions. Serum ELISA results from the 6 mice in the study did not show differentiation between proteins.

TABLE 11

Characterization of derived cell lines derived

| Cell ID | Fusion | Tau-Immunized | Reason for Interest | Isotype |
|---------|--------|---------------|---------------------|---------|
| 1A6     | A      | 352           | Positive for all Tau | IgMx   |
| 1D9     | C      | 412           | Positive for all Tau | IgMx   |
| 14A6    | C      | 412           | Positive for all Tau | IgMx   |
| 17G11   | C      | 412           | Positive for 1, 2, 3 | IgMx   |
| 4G11    | D      | 441           | Positive for 2, 4, 5, 6 | IgAx |
| 2F9     | D      | 441           | Positive for all Tau | IgMx   |

Western blots were performed to determine which isoforms of human tau were targeted by antibodies. 100 g vials of all six isoforms (352, 381, 383, 410, 412, 441) were obtained in lyophilized form. Each vial was rehydrated in 1.0 mL Milli-Q water to give a buffer content of 50 mM MES 100 mM NaCl 0.5 mM EGTA pH 6.8 and from that solution 10 µL was mixed with 90 µL Laemmli Sample Buffer (Bio-Rad #161-0737) containing 2-Mercaptoethanol. These samples were heated at 95° C. for five minutes, and once allowed to cool to room temperature they were spun at RCF 8,000 for ten seconds. 10 µL of each sample was loaded in separate wells of a 4-20% TGX Gel (Bio-Rad #456-1094), and 3 µL of Western Standards (Bio-Rad #161-0376) was added in a separate well. The dilution factor yields 100 ng of total tau protein for each isoform, so as a positive control 100 ng of BSA (Fisher #BP1605-100) was added to a separate well. This gel loading scheme was duplicated on two additional gels, so a total of three gels were run. Two of the gels were used for the blotting procedure, while the third gel was stained to ensure that the target protein was present before transfer. The gel-running apparatus was filled with 1.0 L of a 1× dilution of 10× Tris/Glycine/SDS Running Buffer (Bio-Rad #161-0732). A constant 200 Volts was applied for 30 minutes, or until the dye front from the sample buffer reached the bottom of the gel.

Once the run was complete, the gels were removed from their cases. One gel was placed in Bio-Safe Coomassie G-250 Stain (Bio-Rad #161-0786) for a minimum of 1 hour for imaging. The other two gels were separately placed in the western blot transfer buffer (50 mM Tris/40 mM Glycine/1.3 mM SDS/20% Methanol) for 5-10 minutes. The contents of the gels were then transferred to nitrocellulose membrane at 20 volts for 3 hours using a semi-dry transfer system from Bio-Rad (Bio-Rad #170-3940). Following the transfer, the nitrocellulose membranes were incubated in blocking buffer (50 mM Tris/150 mM NaCl/3.0% BSA, pH 7.4) overnight at 4° C. 50 mM Tris/150 mM NaCl/0.1% Tween 20 was used to wash the membranes thoroughly before they were incubated with the primary antibodies. Each of the above antibodies were prepared at a dilution of 1:5,000 in the wash buffer and incubated with the membranes for 1 hour at 25° C., and then the membranes were washed thoroughly again with the wash buffer (50 mM Tris/150 mM NaCl/0.1% Tween 20). The secondary antibody solution was then prepared using 30 mL wash buffer and 6 µL Goat Anti-Mouse IgG (H+L) HRP-Conjugate (Bio-Rad #170-6516), which gave a 1:5,000 Dilution. To ensure the protein standards were visible during the final step this solution also required the addition of 1.5 µL Precision Protein StrepTactin-HRP Conjugate (Bio-Rad #161-380). The membranes were then incubated in the secondary antibody solution for one hour at 25° C. followed by 3, 5 minute rinses with wash buffer.

In order to image the membranes, 10 mL of Clarity Western ECL Substrate (Bio-Rad #170-5060) was poured on the membranes and incubated for five minutes at 25° C. Following the substrate incubation, the membrane was imaged by exposing it to GE Hyperfilm ECL (Item #45-001-507) for up to 5 minutes.

The selected mAbs except 4G11, an IgA, bound all Tau proteins as visualized by western blot.

Western blot analysis of 4G11 (IgA) is provided in FIG. 2A, showing preferential binding to tau isoforms 381, 410, 412 and 441 respectively. (see also FIG. 6A, FIG. 6B, FIG. 6C and FIG. 6D Western blot analysis of 1A6 (IgM) is provided in FIG. 2B, showing binding to each of the six tau isoforms, respectively. See also FIG. 7.

Example 2—Characterization of 4G11 Monoclonal Antibody

Approximately 3.0×10⁶ hybridoma cells, per clone, were collected and washed via centrifugation. Total RNA was extracted and mRNA was subsequently purified from the pelleted cells. The mRNA was then converted to cDNA utilizing reverse transcriptase.

Specifically designed degenerate primer sets were used to amplify both the heavy and light chain variable regions from the cDNA pool. The exact degenerate primers combinations utilized were chosen on the basis of the antibody isotype (both heavy and light chain isotypes). The primers used for cDNA isolation are as follows:

```
IgG-VH3'
                                        (SEQ ID NO: 50)
(5'-CC CAAGCTTCCAGGGRCCARKGGATARACIGRTGG-3')

IgK-VL3'
                                        (SEQ ID NO: 51)
(5'-CCCAAGCTTACTGGATGGTGGGAAGAT-GGA-3')

Igλ-VL3'
                                        (SEQ ID NO: 52)
(5'-CCCAAGCTTAGCTCYTCWG-WGGAIGGYGGRAA-3')
```

The degenerate primer set used for variable heavy and light chain isolation was obtained from Novagen (Mouse Ig-Primer, cat #69831-3).

The amplified PCR products were gel purified and subsequently extracted. The isolated variable domains were ligated into vectors followed by transformation and plasmid isolation. The final plasmids were sequenced to determine the DNA code of the variable regions.

The following sequences were obtained:

4G11 Heavy Chain amino acid sequence
(SEQ ID NO: 42)
EVQLVESGGGLVQPKGSLKLSCAASGFTFNIYAMNWVRQAPGKGLEWVAR

IRSKSNNYATYYADSMKDRFTISRDDSQSMLYLQMNNLKTEDTAMYYCVR

HGNYYFDYWGQGTTLTVSS

4G11 Heavy Chain DNA sequence:
(SEQ ID NO: 43)
GAGGTGCAGCTTGTTGAGTCTGGTGGAGGATTGGTGCAGCCTAAAGGGT

CATTGAAACTCTCATGTGCAGCCTCTGGATTCACCTTCAATATCTACGC

CATGAACTGGGTCCGCCAGGCTCCAGGAAAGGGTTTGGAATGGGTTGCT

CGCATAAGAAGTAAAAGTAATAATTATGCAACATATTATGCCGATTCAA

TGAAAGACAGGTTCACCATCTCCAGAGATGATTCACAAAGCATGCTCTA

TCTGCAAATGAACAACTTGAAAACTGAGGACACAGCCATGTATTACTGT

GTGAGACATGGTAACTACTACTTTGACTACTGGGGCCAAGGCACCACTC

TCACAGTCTCCTCA

4G11 Light Chain amino acid sequence
(SEQ ID NO: 44)
ENVLTQSPAIMAASLGQKVTMTCSADSSVSSSYLNWYQQKSGASPKPLI

HRTSNLASGVPARFSGSGSGTSYSLTISSVEAEDDATYYCQQWSGYPFI

FTFGSGTKLEIK

4G11 Light Chain DNA sequence:
(SEQ ID NO: 45)
GAAAATGTGCTCACCCAGTCTCCAGCAATAATGGCTGCCTCTCTGGGGC

AGAAGGTCACCATGACCTGCAGTGCCGACTCAAGTGTAAGTTCCAGTTA

CTTGAACTGGTACCAGCAGAAGTCAGGCGCTTCCCCCAAACCCTTGATT

CATAGGACATCCAACCTGGCTTCTGGAGTCCCAGCTCGCTTCAGTGGCA

GTGGGTCTGGGACCTCTTACTCTCTCACAATCAGCAGCGTGGAGGCTGA

AGATGATGCAACTTATTACTGCCAGCAGTGGAGTGGTTACCCATTCATA

TTCACGTTCGGCTCGGGGACAAAGTTGGAAATAAAAC.

Example 3—Epitope Mapping of the 4G11 Monoclonal Antibody

To reconstruct discontinuous epitopes of the target molecule, a library of 426 linear overlapping peptides was synthesized using the tau 441 isoform. This was done using Pepscan's proprietary Chemically Linked Peptides on Scaffolds (CLIPS) technology. CLIPS technology allows to structure peptides into single loops, double loops, triple loops, sheet-like folds, helix-like folds, and combinations thereof. CLIPS templates were coupled to side-chain thiol groups of cysteine residues. The side-chains of (multiple) cysteines in the peptides were coupled to one or two CLIPS templates. More specifically, a 0.5 mM solution of the T2 CLIPS template 1,3-bis (bromomethyl) benzene was dissolved in ammonium bicarbonate (20 mM, pH 7.9)/acetonitrile 1:1 (v/v). This solution was added to the peptide arrays. The CLIPS template binds to the side-chains of two cysteines as present in the solid-phase bound peptides of the arrays (455 well-plate with 3 µl wells). The peptide arrays were gently shaken for 30 to 60 minutes while completely covered in the aforementioned solution. Finally, the peptide arrays were washed extensively with an excess of $H_2O$, and sonicated in a disrupt-buffer containing 1% SDS/0.1% beta-mercaptoethanol in PBS (pH 7.2) at 70° C. for 30 minutes, followed by sonication in $H_2O$ for another 45 minutes. The T3 CLIPS carrying peptides were prepared likewise but with three cysteines.

The binding of antibody to each of the synthesized peptides was tested in a PEPSCAN-based ELISA. In this assay, the peptide arrays were incubated with primary antibody solution (overnight at 4° C.). After washing, the peptide arrays were incubated with a 1/1000 dilution of an antibody peroxidase conjugate (SBA, cat. nr. 2010-05) for one hour at 25° C. After washing, the peroxidase substrate 2,2'-azino-di-3-ethylbenzthiazoline sulfonate (ABTS) and 2 µl/ml of 3% $H_2O_2$ were added. After one hour, the color development was measured. The color development was quantified with a charge coupled device (CCD) camera and an image processing system.

The values obtained from the CCD camera range from 0 to 3000 mAU, similar to a standard 96-well plate ELISA-reader. The results were quantified and stored into the Peplab database. Occasionally, a well may contain an air-bubble resulting in a false positive value. To avoid this issue, cards were manually inspected, and any values caused by an air-bubble are scored as 0.

To assess the quality of the synthesized peptides, a separate set of positive and negative control peptides were synthesized in parallel. Such peptide sets were screened with antibody 57.9 (ref Posthumus et al., J. Virol. 1990, 64: 3304-3309).

Antibody binding depends on a combination of factors, which include the concentration of the antibody, and also the amount and nature of competing proteins in the ELISA buffer. The pre-coating conditions (i.e the specific treatment of the peptide arrays prior to incubation with the experimental sample) also affect the binding of the antibody. Detailed conditions for the screening are summarized in Table 12. For the ELISA buffer and the pre-conditioning (SQ), the values depicted in the Table indicate the relative amount of competing protein (i.e a combination of horse serum and ovalbumin). P/T indicates a PBS/Tween mix without competing protein.

TABLE 12

| Screening Conditions | | | |
|---|---|---|---|
| Sample | Dilution | Sample buffer | Preconditioning |
| 4G11 (1) | 1 ug/ml | 0.1% SQ | 0.1% SQ |
| 4G11 (1) | 1 ug/ml | SQ | SQ |

Figure 3:
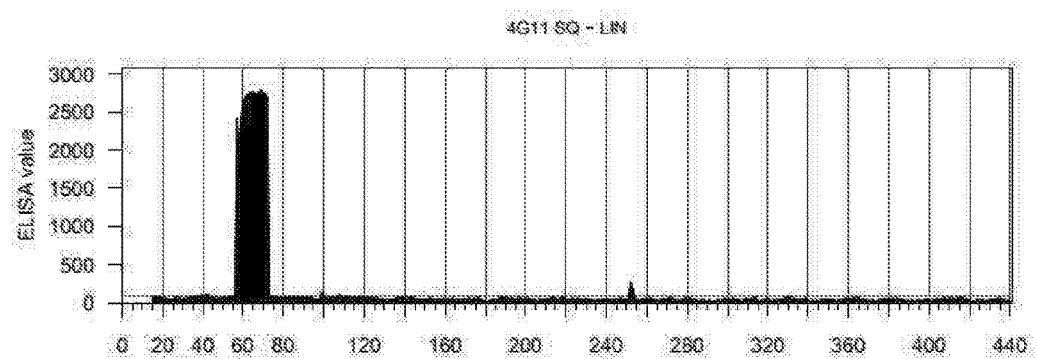
FIG. 3 provides a graphic illustration of the epitope mapping results for the antibody 4G11 tested under high stringency conditions. A clear peak containing the epitope core EEPGSETS (SEQ ID NO: 7) can be discerned.

Antibody 4G11 yielded a clean and saturated signal when tested under high stringency conditions on the linear 15-mer Tau array (see FIG. 3). The linear epitope core was EEPG-SETS (SEQ ID NO:7).

Example 4—4G11 Binding to Tau Isoforms

Antibody 4G11 was tested in an ELISA against 100 ng and 50 ng of the six human Tau isoform using antibodies dilutions of 1:1,000 and 1:10,000. Both 4G11 stored at −80° C. as well as a lyophilized form stored at ambient temperature were compared in this assay and the results are provided in FIGS. 6A-D (the left bar for each isoform are the results of the antibody stored at −80° C. and the right bar for each isoform is the lyophilized form, stored at 25° C.

Based on the results shown, a dilution of 1:1,000 is recommended in TBST (0.1% Tween 20) buffer containing 1.0% BSA. Furthermore the results show that the 4G11 antibody may be safely lyophilized and provided in a state of suspended animation without concern for loss of activity. The lyophilized 4G11 for may be either stored at room temperature until use, or rehydrated to make smaller aliquots that are stored at −80° C.

Example 5—Characterization of 1A6 Monoclonal Antibody

Approximately $3.0 \times 10^6$ hybridoma cells, per clone, were collected and washed via centrifugation. Total RNA was extracted and mRNA was subsequently purified from the pelleted cells. The mRNA was then converted to cDNA utilizing reverse transcriptase.

Specifically designed degenerate primer sets were used to amplify both the heavy and light chain variable regions from the cDNA pool. The exact degenerate primers combinations utilized were chosen on the basis of the antibody isotype (both heavy and light chain isotypes). Generation of such primer sequences using standard methods is readily apparent to the skilled artisan.

The amplified PCR products were gel purified and subsequently extracted. The isolated variable domains were ligated into vectors followed by transformation and plasmid isolation. The final plasmids were sequenced to determine the DNA code of the variable regions.

The following sequences were obtained:

```
1A6 Heavy Chain amino acid sequence:
                                        (SEQ ID NO: 46)
DVQLVESGGGLVQPGGSRKLSCAASGFTFSSFGMHWVRQVPEKGLEWVAY

ISSGSSTIYYADTVKGRFTISRDNPKNTLFLQMTSLRSEDTAMYYCASNQ

SPTGQGTLVTVSA.

1A6 Heavy Chain DNA sequence:
                                        (SEQ ID NO: 47)
GATGTGCAGCTGGTGGAGTCTGGGGGAGGCTTAGTGCAGCCTGGAGGGTC

CCGGAAACTCTCCTGTGCAGCCTCTGGATTCACTTTCAGTAGCTTTGGAA

TGCACTGGGTTCGTCAGGTTCCAGAGAAGGGGCTGGAGTGGGTCGCATAC

ATTAGTAGTGGCAGTAGTACCATCTACTATGCAGACACAGTGAAGGGCCG

ATTCACCATCTCCAGAGACAATCCCAAGAACACCCTGTTCCTGCAAATGA

CCAGTCTAAGGTCTGAGGACACGGCCATGTATTACTGTGCAAGTAACCAA

TCCCCTACGGGGTTTGCTTACTGGGGCCAAGGGACTCTGGTCACTGTCTC

TGCA.

1A6 Light Chain amino acid sequence:
                                        (SEQ ID NO: 48)
DVVMTQTPLSLPVSLGDQASISCRSSQSLVHSNGNTYLHWYLQKPGQSPK

LLIYKVSNRFSGVPDRFSGSGSGTDFTLKISRVEAEDLGVYFCSQSTHVP

LTFGAGTKLELK.

1A6 Light Chain DNA sequence:
                                        (SEQ ID NO: 49)
GATGTTGTGATGACCCAAACTCCACTCTCCCTGCCTGTCAGTCTTGGAGA

TCAAGCCTCCATCTCTTGCAGATCTAGTCAGAGCCTTGTACACAGTAATG

GAAACACCTATTTACATTGGTACCTGCAGAAGCCAGGCCAGTCTCCAAAG

CTCCTAATCTACAAAGTTTCCAACCGATTTTCTGGGGTCCCAGACAGGTT

CAGTGGCAGTGGATCAGGGACAGATTTCACACTCAAGATCAGCAGAGTGG
```

-continued
```
AGGCTGAGGATCTGGGAGTTTATTTCTGCTCTCAAAGTACACATGTTCCT

CTCACGTTCGGTGCTGGGACCAAGCTGGAGCTGAAA.
```

Example 6—Epitope Mapping of the 1A6 Monoclonal Antibody

To reconstruct discontinuous epitopes of the target molecule, a library of 426 linear overlapping peptides was synthesized using the tau 441 isoform. This was done using Pepscan's proprietary Chemically Linked Peptides on Scaffolds (CLIPS) technology. CLIPS technology allows to structure peptides into single loops, double loops, triple loops, sheet-like folds, helix-like folds, and combinations thereof. CLIPS templates were coupled to side-chain thiol groups of cysteine residues. The side-chains of (multiple) cysteines in the peptides were coupled to one or two CLIPS templates. More specifically, a 0.5 mM solution of the T2 CLIPS template 1,3-bis (bromomethyl) benzene was dissolved in ammonium bicarbonate (20 mM, pH 7.9)/acetonitrile 1:1 (v/v). This solution was added to the peptide arrays. The CLIPS template binds to the side-chains of two cysteines as present in the solid-phase bound peptides of the arrays (455 well-plate with 3 µl wells). The peptide arrays were gently shaken for 30 to 60 minutes while completely covered in the aforementioned solution. Finally, the peptide arrays were washed extensively with an excess of $H_2O$, and sonicated in a disrupt-buffer containing 1% SDS/0.1% beta-mercaptoethanol in PBS (pH 7.2) at 70° C. for 30 minutes, followed by sonication in $H_2O$ for another 45 minutes. The T3 CLIPS carrying peptides were prepared likewise but with three cysteines.

The binding of antibody to each of the synthesized peptides was tested in a PEPSCAN-based ELISA. In this assay, the peptide arrays were incubated with primary antibody solution (overnight at 4° C.). After washing, the peptide arrays were incubated with a 1/1000 dilution of an antibody peroxidase conjugate (SBA, cat. nr. 2010-05) for one hour at 25° C. After washing, the peroxidase substrate 2,2'-azino-di-3-ethylbenzthiazoline sulfonate (ABTS) and 2 µl/ml of 3% $H_2O_2$ were added. After one hour, the color development was measured. The color development was quantified with a charge coupled device (CCD) camera and an image processing system.

The values obtained from the CCD camera range from 0 to 3000 mAU, similar to a standard 96-well plate ELISA-reader. The results were quantified and stored into the Peplab database. Occasionally, a well may contain an air-bubble resulting in a false positive value. To avoid this issue, cards were manually inspected, and any values caused by an air-bubble were scored as 0.

To assess the quality of the synthesized peptides, a separate set of positive and negative control peptides were synthesized in parallel. Such peptide sets were screened with antibody 57.9 (ref Posthumus et al., J. Virol. 1990, 64: 3304-3309).

Antibody binding depends on a combination of factors, which include the concentration of the antibody, and also the amount and nature of competing proteins in the ELISA buffer. The pre-coating conditions (i.e the specific treatment of the peptide arrays prior to incubation with the experimental sample) also affect the binding of the antibody. Detailed conditions for the screening are summarized in Table 13. For the ELISA buffer and the pre-conditioning (SQ), the values depicted in the Table indicate the relative amount of competing protein (i.e a combination of horse serum and ovalbumin). P/T indicates a PBS/Tween mix without competing protein.

TABLE 13

Screening Conditions

| Sample | Dilution | Sample buffer | Preconditioning |
|---|---|---|---|
| 1A6 (1) | 1 ug/ml | 0.1% SQ | 0.1% SQ |
| 1A6 (1) | 1 ug/ml | P/Tw | P/Tw |

Figure 4:
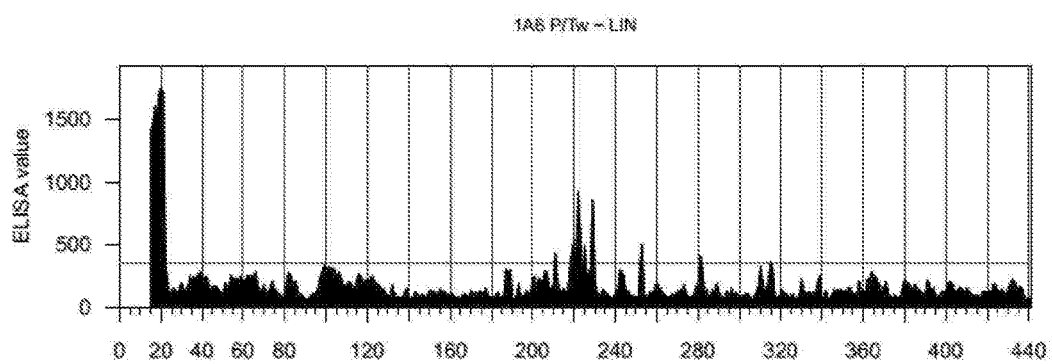
FIG. 4 provides a graphic illustration of the epitope mapping results for the antibody 1A6 tested under low stringency conditions. A peak containing the epitope core EFEVMEDHAGT (SEQ ID NO: 8) can be discerned, and additional signal is picked up near residue 220, LPTPPT (SEQ ID NO: 9). This implies a conformational or complex epitope.
Figure 6A:
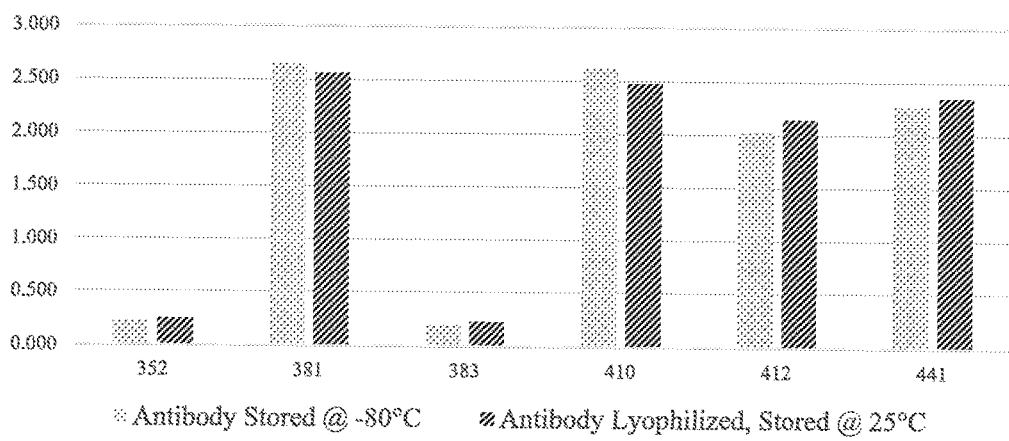
FIGS. 6A, 6B, 6C and 6D provide graphic illustrations of ELISA results of the 4G11 mAb using the following Tau isoforms: 352, 381, 383, 410, 412, and 441. More specifically, the 4G11 mAb was tested in an ELISA against 100 ng of each of the Tau isoforms at a 1:1,000 antibody dilution (FIG. 6A); against 100 ng of each of the Tau isoforms at a 1:10,000 antibody dilution (FIG. 6B); against 50 ng of each of the Tau isoforms at a 1:1,000 antibody dilution (FIG. 6C); and against 50 ng of each of the Tau isoforms at a 1:10,000 antibody dilution (FIG. 6D). Binding was exhibited with all tested isoforms at all dilutions, particularly of tau381, tau412, tau410, and tau441. The highest binding levels were found using 100 ng of the tau isoform with an antibody dilution of 1:1,000.
Figure 6B:
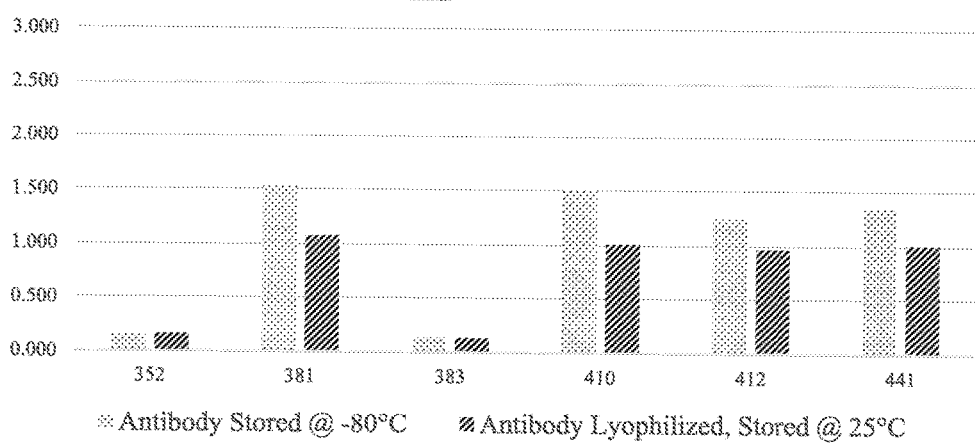
Figure 6C:
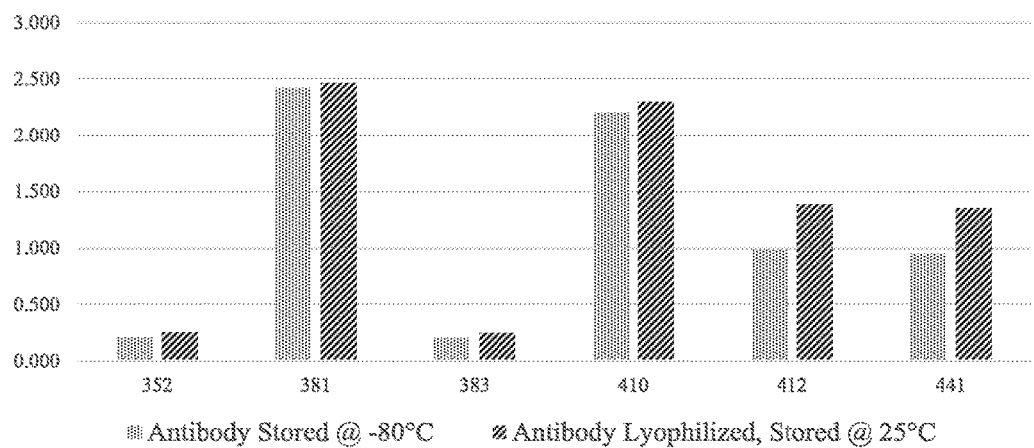
Figure 6D:
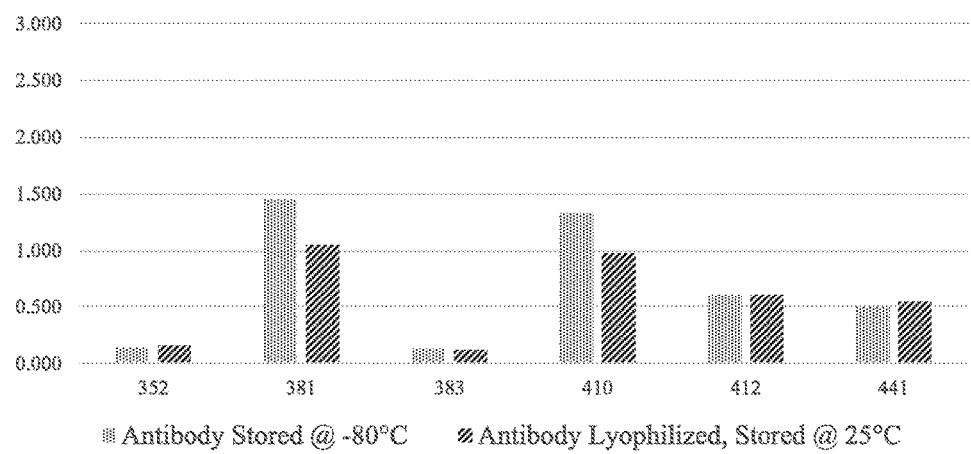

Antibody 1A6 showed a low signal-to-noise ratio when tested under normal stringency conditions. When the competing protein was omitted from the sample buffer, clear binding to peptides containing the common core EFE-VMEDHAGT (SEQ ID NO: 8) was observed (see FIG. 4). However, under these conditions, additional binding near the residue 220 (core=LPTPPT—SEQ ID NO: 9) is also seen. This may imply a complex or conformational epitope.

Example 7—1A6 Binding to Tau Isoforms

Figure 7:
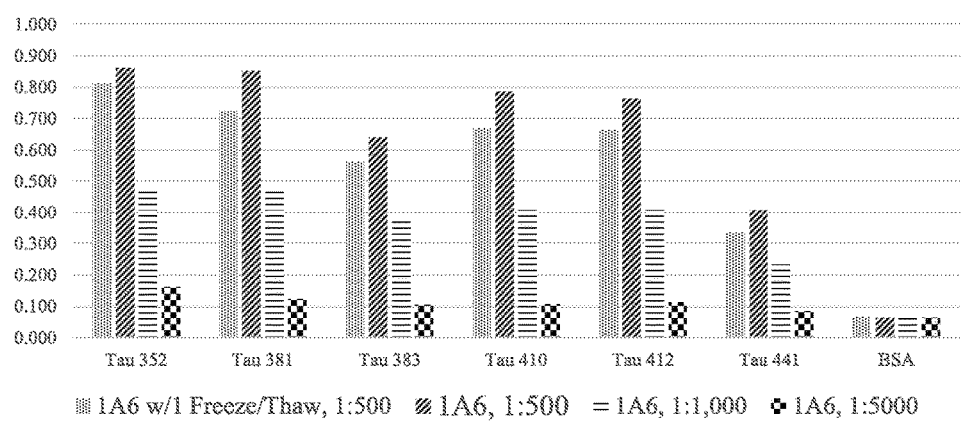
FIG. 7 provides a graphic illustration of ELISA result of the 1A6 mAb using the following Tau isoforms: 352, 381, 383, 410, 412, and 441 and BSA as a control. More specifically, 1A6 was tested in an ELISA against 100 ng of the six human Tau isoforms using antibody dilutions of 1:500, 1:1,000 and 1:5,000. Initial stability testing, as seen in the left-most bar, indicates a slight loss in activity upon putting the antibody through an extra freeze/thaw cycle.

Antibody 1A6 was tested in an ELISA against 100 ng of the six human Tau isoforms, using antibody dilutions of 1:500, 1:1,000 and 1:5,000. The results are shown in FIG. 7. The left-most bar for each isoform represents a 1:500 dilution with 1 freeze to thaw cycle; the middle-left bar represents the mAb at a 1:500 dilution; the middle right bar represents the mAb at a 1:1,000 dilution and the right-most bar represents the mAb at a 1:5,000 dilution. Binding was exhibited with all tested isoforms. Initial stability testing, as seen by the left most line, indicates a slight loss in activity upon putting the antibody through an extra freeze/thaw cycle.

Example 8—Tau 4G11 and 1A6 CDR Regions

The complementarity determining regions (CDR) within the heavy and light chains for the Tau 4G11 and Tau 1A6 antibodies were determined using the Chothia Method (Chothia et al., "Canonical structures for the hypervariable regions of immunoglobulins," J. Mol. Biol. 1987, Aug. 20; 196(4): 901-917) and Kabat Method (Kabat et al., "Sequences of Proteins of Immunological Interest," U.S. Department of Health and Human Services, 1983). Below, Tables 14-19 provides the sequences defining the CDRs in the heavy and light chains of both Tau 4G11 and Tau 1A6. Also provided are the entire amino acid sequences of the heavy and light chains, where the CDR regions are underlined:

TABLE 14

Chothia Heavy Chain CDR Analysis for 4G11

| | Sequence | Residues | Length |
|---|---|---|---|
| CDR-H1 | GFTFNIY (SEQ ID NO: 10) | 26-32 | 7 |
| CDR-H2 | RSKSNNYA (SEQ ID NO: 11) | 52-59 | 8 |
| CDR-H3 | HGNYYFDY (SEQ ID NO: 12) | 101-108 | 8 |

TABLE 15

Kabat Heavy Chain CDR Analysis for 4G11

| | Sequence | Residues | Length |
|---|---|---|---|
| CDR-H1 | IYAMN (SEQ ID NO: 13) | 31-35 | 5 |
| CDR-H2 | RIRSKSNNYATYYADSMKD (SEQ ID NO: 14) | 50-68 | 19 |
| CDR-H3 | HGNYYFDY (SEQ ID NO: 12) | 101-108 | 8 |

TABLE 16

Chothia and Kabat Light Chain CDR Analysis for 4G11

| | Sequence | Residues | Length |
|---|---|---|---|
| CDR-L1 | SADSSVSSSYLN (SEQ ID NO: 15) | 24-35 | 12 |
| CDR-L2 | RTSNLAS (SEQ ID NO: 16) | 51-57 | 7 |
| CDR-L3 | QQWSGYPFIFT (SEQ ID NO: 17) | 90-100 | 11 |

TABLE 17

Chothia Heavy Chain CDR Analysis for 1A6

| | Sequence | Residues | Length |
|---|---|---|---|
| CDR-H1 | GFTFSSF (SEQ ID NO: 18) | 26-32 | 7 |
| CDR-H2 | SSGSST (SEQ ID NO: 19) | 52-57 | 6 |
| CDR-H3 | NQSPTGFAY (SEQ ID NO: 20) | 99-107 | 9 |

TABLE 18

Kabat Heavy Chain CDR Analysis for 1A6

| | Sequence | Residues | Length |
|---|---|---|---|
| CDR-H1 | SFGMH (SEQ ID NO: 21) | 31-35 | 5 |
| CDR-H2 | YISSGSSTIYYADTVKG (SEQ ID NO: 22) | 50-66 | 17 |
| CDR-H3 | NQSPTGFAY (SEQ ID NO: 20) | 99-107 | 9 |

TABLE 19

Chothia and Kabat Light Chain CDR Analysis for 1A6

| | Sequence | Residues | Length |
|---|---|---|---|
| CDR-L1 | RSSQSLVHSNGNTYLH (SEQ ID NO: 23) | 24-39 | 16 |
| CDR-L2 | KVSNRFS (SEQ ID NO: 24) | 55-61 | 7 |
| CDR-L3 | SQSTHVPLT (SEQ ID NO: 25) | 94-102 | 9 |

Sequence 1: Tau 4G11 Heavy Chain with Chothia CDRs Highlighted
(SEQ ID NO: 42)
EVQLVESGGGLVQPKGSLKLSCAAS<u>GTFFNIY</u>AMNWVRQAPGKGLEWVAR

IRSKSNNYATYYADSMKDRFTISRDDSQSMLYLQMNNLKTEDTAMYYCVR

<u>HGNYYFDY</u>WGQGTTLTVSS

Sequence 2: Tau 4G11 Heavy Chain with Kabat CDRs Highlighted
(SEQ ID NO: 42)
EVQLVESGGGLVQPKGSLKLSCAASGFTFN<u>IYAMN</u>WVRQAPGKGLEWVA<u>R IRSKSNNYATYYADSMKD</u>RFTISRDDSQSMLYLQMNNLKTEDTAMYYCVR <u>HGNYYFDY</u>WGQGTTLTVSS Sequence 3: Tau 4G11 Light Chain with Chothia and Kabat CDRs Highlighted
(SEQ ID NO: 44)
ENVLTQSPAIMAASLGQKVTMTC<u>SADSSVSSSYLN</u>WYQQKSGASPKPLIH <u>RTSNLAS</u>GVPARFSGSGSGTSYSLTISSVEAEDDATYYC<u>QQWSGYPFIFT</u>

FGSGTKLEIK

Sequence 4: Tau 1A6 Heavy Chain with Chothia CDRs Highlighted
(SEQ ID NO: 46)
DVQLVESGGGLVQPGGSRKLSCAAS<u>GFTFSSF</u>GMHWVRQVPEKGLEWVAY <u>ISSGSSTI</u>YYADTVKGRFTISRDNPKNTLFLQMTSLRSEDTAMYYCASN<u>Q SPTGFAY</u>WGQGTLVTVSA Sequence 5: Tau 1A6 Heavy Chain with Kabat CDRs Highlighted
(SEQ ID NO: 46)
DVQLVESGGGLVQPGGSRKLSCAASGFTFS<u>SFGMH</u>WVRQVPEKGLEWVAY<u>

ISSGSSTIYYADTVKG</u>RFTISRDNPKNTLFLQMTSLRSEDTAMYYCASN<u>Q

SPTGFAY</u>WGQGTLVTVSA

Sequence 6: Tau 1A6 Light Chain with Chothia and Kabat CDRs Highlighted
(SEQ ID NO: 48)
DVVMTQTPLSLPVSLGDQASISC<u>RSSQSLVHSNGNTYLH</u>WYLQKPGQSPK LLIY<u>KVSNRFS</u>GVPDRFSGSGSGTDFTLKISRVEAEDLGVYFC<u>SQSTHVP LT</u>FGAGTKLELK.

DEPOSIT OF HYBRIDOMA CELL LINES

The following hybridomas were deposited with the American Type Culture Collection (ATCC, Manassas, Va.) on Feb. 24, 2015, and assigned the following ATCC designation:

1. Hybridoma strain Tau-1A6 ("h1A6") producing monoclonal antibody 1A6 was assigned ATCC designation PTA-122038.
2. Hybridoma strain Tau-4G11 ("h4G11") producing monoclonal antibody 4G11 was assigned ATCC designation PTA-122039.

---

What is claimed is:

1. An isolated antibody or fragment thereof that specifically interacts and shows measurable binding affinity to an epitope of at least one tau protein isoform, the isolated antibody or fragment comprising variable light chain complementarity determining regions that are SEQ ID NO: 15-CDR 1; SEQ ID NO: 16-CDR 2; and SEQ ID NO: 17-CDR 3 and further comprising variable heavy chain complementarity determining regions that are SEQ ID NO: 10-CDR 1; SEQ ID NO: 11-CDR 2; and SEQ ID NO: 12-CDR 3, or in the alternative SEQ ID NO: 13-CDR 1; SEQ ID NO: 14-CDR 2; and SEQ ID NO: 12-CDR 3.

2. The isolated antibody or fragment thereof of claim 1, wherein the tau isoform is selected from the group consisting of tau381, tau412, tau410, tau441.

3. The isolated antibody or fragment thereof of claim 1 that specifically interacts and shows measurable affinity to SEQ ID NO: 7 of a tau protein.

4. The isolated antibody or fragment thereof of claim 1, wherein said antibody is selected from the group consisting of a monoclonal antibody, a polyclonal antibody, a recombinant antibody, a chimeric antibody and a humanized antibody.

5. The isolated antibody or fragment thereof of claim 1, wherein said antibody is raised in a mammal.

6. A method of modulating tau activity in a cell comprising administering to a mammal an effective amount of the antibody of claim 1.

7. A pharmaceutical formulation comprising an antibody of claim 1 and a pharmaceutically acceptable carrier.

8. A method of treating a neurodegenerative tauopathy in a subject in need thereof, comprising administering a therapeutically effective amount of the antibody, or fragment thereof, of claim 1.

9. A recombinant vector comprising a polynucleotide encoding an antibody of claim 1.

10. A host cell comprising the recombinant vector of claim 9.

11. A method of diagnosing or monitoring the progression of a neurodegenerative tauopathy in a subject, comprising:
  (a) providing a biological sample from a patient to be diagnosed and contacting the biological sample with an antibody of claim 1;
  (b) measuring the level of pathologically modified or aggregated tau protein in a biological sample from the subject to be diagnosed with the antibody of any of claim 1 by IHC; and, (c) comparing the level of modified or aggregated tau protein to a reference standard that indicates the level of the pathologically modified or aggregated tau in one or more control subjects, wherein a difference or similarity between the level of pathologically modified or aggregated tau and the reference standard indicates that the subject has a neurodegenerative tauopathy.

12. The method of claim 11, wherein the neurodegenerative tauopathy is Alzheimer's disease.

13. A method for in vivo detection of or targeting a therapeutic or diagnostic agent to tau in the human or animal body, comprising administering a composition comprising the antibody of claim 1 attached to a therapeutic or diagnostic agent.

14. The method of claim 13, wherein the in vivo detection comprises positron emission tomography (PET), single photon emission tomography (SPECT), near infrared (NIK) optical imaging or magnetic resonance imaging (MRI).

15. A hybridoma which is hybridoma h4G11, deposited with the American Type Culture Collection (ATCC) on Feb. 24, 2015 and assigned ATCC designation PTA-122039.

16. An isolated antibody produced by the hybridoma of claim 15.

17. An isolated antibody or fragment thereof that specifically interacts and shows measurable binding affinity to an epitope of at least one tau protein isoform, the isolated antibody or fragment comprising a variable light chain comprising an amino acid sequence of at least 90% identity to SEQ ID NO: 44, and a variable heavy chain comprising an amino acid sequence of at least 90% identity to SEQ ID NO: 42.

18. The isolated antibody or fragment thereof of claim 17, wherein said antibody is selected from the group consisting of a monoclonal antibody, a polyclonal antibody, a recombinant antibody, a chimeric antibody and a humanized antibody.

19. A pharmaceutical formulation comprising an antibody of claim 17 and a pharmaceutically acceptable carrier.

20. A method of treating a neurodegenerative tauopathy in a subject in need thereof, comprising administering a therapeutically effective amount of the antibody, or fragment thereof, of claim 17.

* * * * *